US009556244B2

(12) United States Patent
Guerrero et al.

(10) Patent No.: US 9,556,244 B2
(45) Date of Patent: *Jan. 31, 2017

(54) VACCINATION OF ANIMALS TO ELICIT A PROTECTIVE IMMUNE RESPONSE AGAINST TICK INFESTATIONS AND TICK-BORNE PATHOGEN TRANSMISSION

(71) Applicant: The United States of America, as Represented by the Secretary of Agriculture, Washington, DC (US)

(72) Inventors: Felicito Guerrero, Boerne, TX (US); Adalberto A. Perez de Leon, Wake Forest, NC (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 258 days.

This patent is subject to a terminal disclaimer.

(21) Appl. No.: 14/220,909

(22) Filed: Mar. 20, 2014

(65) Prior Publication Data

US 2014/0212452 A1 Jul. 31, 2014

Related U.S. Application Data

(62) Division of application No. 13/479,486, filed on May 24, 2012, now Pat. No. 8,722,063.

(51) Int. Cl.
*C07K 14/435* (2006.01)
*A61K 39/00* (2006.01)

(52) U.S. Cl.
CPC ..... *C07K 14/43563* (2013.01); *A61K 39/0003* (2013.01); *C07K 14/43527* (2013.01); *A61K 2039/53* (2013.01); *A61K 2039/552* (2013.01); *A61K 2039/55566* (2013.01)

(58) Field of Classification Search
None
See application file for complete search history.

(56) References Cited

U.S. PATENT DOCUMENTS

| 2004/0052807 A1 | 3/2004 | Salcedo et al. |
| 2007/0031411 A1 | 2/2007 | Trimnell et al. |
| 2010/0278752 A1 | 11/2010 | Kotsyfakis et al. |

OTHER PUBLICATIONS

Ball, Andrew et al., "Identification, functional characterization and expression patterns of a water-specific aquaporin in the brown dog tick, *Rhipicephalus sanguineus*", Insect Biochemistry and Molecular Biology, (2009) 39:105-112.
Seixas, Adriana et al., "Rhipicephalus (Boophilus) microplus embryo proteins as target for tick vaccine" (2012) 148:149-156.
Rachinsky, Anna, et al., "Proteomic profiling of Rhipicephalus (Boophilus) microplus midgut responses to infection with Babesia bovis", Veterinary Parasitology, 152, 2008, pp. 294-313.
Guerrero, F.D., et al., "BmiGI: A database of cDNAs expressed in Boophilus microplus, the tropical/southern cattle tick", Insect Biochemistry and Molecular Biology, 35, 2005, pp. 585-595.
Nuttall, P.A., et al., "Exposed and concealed antigens as vaccine targets for controlling ticks and tick-borne diseases", Parasite Immunology, 2006, 28, pp. 155-163.
Sunter, Jack D., et al., "A novel SINE family occurs frequently in both genomic DNA and transcribed sequences in ixodid ticks of the arthropod sub-phylum Chelicerata", Gene, 415, 2008, pp. 13-22.
Guerrero, Felix D., et al., "Sequencing a New Target Genome: The Boophilus microplus (Acari: Ixodidae) Genome Project", Journal of Medical Entomology, vol. 43, No. 1, Jan. 2006, pp. 9-16.
Guerrero, Felix D., et al., "Use of an Allelle-Specific Polymerase Chain Reaction Assay to Genotype Pyrethroid Resistant Strains of Boophilus microplus (Acari: Ixodidae)", Journal of Medical Entomology, vol. 38, No. 1, Jan. 2001, pp. 44-50.
Campbell, Ewan M., et al., "Role of an aquaporin in the sheep tick *Ixodes ricinus*: Assessment as a potential control target", International Journal for Parasitology, 40, 2010, pp. 15-23.

*Primary Examiner* — Robert A Zeman
(74) *Attorney, Agent, or Firm* — John D. Fado; David L. Marks

(57) ABSTRACT

Two antigenic and immunogenic proteins of the cattle tick, *Rhipicephalus microplus*, and the genes encoding these proteins, are effective for eliciting a protective immune response that controls and prevents infestations of bovines and other livestock by the tick. The proteins isolated from the cattle tick include an aquaporin protein and a TC5777 gut membrane protein. Each of the proteins elicit an immunoprotective response in livestock to the cattle tick, and can be formulated and administered as vaccines. Alternatively, the isolated DNA sequences which encode these proteins can be incorporated into nucleic acid constructs which could be utilized as DNA vaccines. The nucleic acid constructs can also be used for the transformation of cells and the production of recombinant proteins. Induction of the protective immune response controls and prevents infestations of the treated animals with the tick, thereby protecting them against tick-borne pathogen transmission.

16 Claims, 8 Drawing Sheets

Figure 1A
MKIENLLIRQLINEFLGTMILITIGDSIMAIIIAGDNESLAACVGPLGWGVAIYVAVQISGGVS
SHLNPAVTLAQASVRKFPIAKVPLYFAAQYLGGFVGAALVFATYKDAIEHFDQGIRQVTGE
KATAGIFATYPRPHVSTLTCFIDQVIATGIMMVCVEAIGDTRNFGGIPPHIHPICLGLMIMAI
IFSFAYNCMCPL Figure 1B
MRFPSIFTAVLFAASSALAAPVNTTTEDETAQIPAEAVIGYSDLEGDFDVAVLPFSNSTNN
GLLFINTTIASIAAKEEGVSLEKREAEAEFMKIENLLIRQLINEFLGTMILITIGDSIMAIIIAG
DNESLAACVGPLGWGVAIYVAVQISGGVSSHLNPAVTLAQASVRKFPIAKVPLYFAAQYLG
GFVGAALVFATYKDAIEHFDQGIRQVTGEKATAGIFATYPRPHVSTLTCFIDQVIATGIMM
VCVEAIGDTRNFGGIPPHIHPICLGLMIMAIIFSFAYNCMCPAAASFLEQKLISEEDLNSAVD
HHHHHH*

Figure 1C
MEIENLLIRQLINEFLGTMILITIGDSIMAIIIAGDNESLAACVGPLGWGVAIYVAVQISGGVS
SHLNPAVTLAQASVRKFPIAKVPLYFAAQYLGGFVGAALVFATYKDAIEHFDQGIRQVTGE
KATAGIFATYPRPHVSTLTCFIDQVIATGIMMVCVEAIGDTRNFGGIPPHIHPICLGLMIMAI
IFSFAYNCMCLESRGPFEQKLISEEDLNMHTGHHHHHH*

Figure 2A

AAGCAGTGGTATCAACGCAGAGTACGCGGGGGGGCTGGGAAAAGCTGCTAGCATCAACT
CGGCTTCTAGCTTGGGGTCTCGCACCGCGCCTCGAGCCCGACCAGCCTGCGGTGGCGCCGT
CTCGCTGAAAGGGGGAAAGAGGAAAGAGAAAGAAGAAAAGAAAAATATCGCCGGCATCG
GCGACGAAGGCGGAGCAGCAATGCGATCGTCAGAGCACGCATTTCGACGGTGAGATTCGG
AAGCTCGAAGGCGTCGCCGGCACTGCGAGAAAGCCGGTGAAGTACTTTGGGACCGCCGCG
TAGGCGTCTTGACAGTCCGCTCCCGAGGCAACGACGACACGCTCCAAG<u>ATGAAGATCGAG</u>
<u>AACCTGCTCATACGGCAGCTCATCAACGAGTTCCTCGGAACAATGATTCTAATTACTATC</u>
<u>GGCGACTCCATCATGGCCATCATCATCGCCGGTGACAACGAGTCTCTGGCTGCTTGCGTG</u>
<u>GGGCCCTTGGGATGGGGCGTCGCCATCTACGTGGCCGTGCAAATCTCCGGAGGAGTCTCG</u>
<u>TCCCACCTGAATCCTGCCGTGACGCTGGCCCAGGCGTCCGTGCGCAAGTTTCCGATCGCCA</u>
<u>AAGTGCCGCTATACTTCGCGGCTCAGTACCTGGGTGGCTTCGTCGGTGCGGCGCTCGTGT</u>
<u>TTGCCACCTACAAAGACGCTATTGAACACTTCGACCAGGGAATCCGCCAAGTGACGGGAG</u>
<u>AGAAGGCCACGGCTGGTATATTTGCAACTTACCCCAGACCACACGTCTCCACTCTGACCT</u>
<u>GCTTCATTGATCAGGTCATCGCAACGGGCATAATGATGGTGTGCGTCGAGGCCATCGGCG</u>
<u>ACACTCGCAACTTCGGCGGCATTCCGCCGCACATTCACCCAATCTGCTTGGGTCTCATGA</u>
<u>TCATGGCTATTATCTTCAGTTTCGCCTACAACTGCATGTGCCCGCTC</u>

Figure 2B

ATGAGATTTCCTTCAATTTTTACTGCTGTTTTATTCGCAGCATCCTCCGCATTAGCTGCT
CCAGTCAACACTACAACAGAAGATGAAACGGCACAAATTCCGGCTGAAGCTGTCATCGGT
TACTCAGATTTAGAAGGGGATTTCGATGTTGCTGTTTTGCCATTTTCCAACAGCACAAAT
AACGGGTTATTGTTTATAAATACTACTATTGCCAGCATTGCTGCTAAAGAAGAAGGGGT
ATCTCTCGAGAAAAGAGAGGCTGAAGCTGAATTC<u>ATGAAGATCGAGAACCTGCTCATAC</u>
<u>GGCAGCTCATCAACGAGTTCCTCGGAACAATGATTCTAATTACTATCGGCGACTCCATCA</u>
<u>TGGCCATCATCATCGCCGGTGACAACGAGTCTCTGGCTGCTTGCGTGGGGCCCTTGGGAT</u>
<u>GGGGCGTCGCCATCTACGTGGCCGTGCAAATCTCCGGAGGAGTCTCGTCCCACCTGAATC</u>
<u>CTGCCGTGACGCTGGCCCAGGCGTCCGTGCGCAAGTTTCCGATCGCCAAAGTGCCGCTAT</u>
<u>ACTTCGCGGCTCAGTACCTGGGTGGCTTCGTCGGTGCGGCGCTCGTGTTTGCCACCTACA</u>
<u>AAGACGCTATTGAACACTTCGACCAGGGAATCCGCCAAGTGACGGGAGAGAAGGCCACG</u>
<u>GCTGGTATATTTGCAACTTACCCCAGACCACACGTCTCCACTCTGACCTGCTTCATTGAT</u>
<u>CAGGTCATCGCAACGGGCATAATGATGGTGTGCGTCGAGGCCATCGGCGACACTCGCAAC</u>
<u>TTCGGCGGCATTCCGCCGCACATTCACCCAATCTGCTTGGGTCTCATGATCATGGCTATT</u>
<u>ATCTTCAGTTTCGCCTACAACTGCATGTGCCCG</u>GCGGCCGCCAGCTTTCTAGAACAAAAA
CTCATCTCAGAAGAGGATCTGAATAGCGCCGTCGACCATCATCATCATCATCATTGA

Figure 2C

AAGATGGAGATCGAGAACCTGCTCATACGGCAGCTCATCAACGAGTTCCTCGGAACAATG
ATTCTAATTACTATCGGCGACTCCATCATGGCCATCATCATCGCCGGTGACAACGAGTCT
CTGGCTGCTTGCGTGGGGCCCTTGGGATGGGGCGTCGCCATCTACGTGGCCGTGCAAATC
TCCGGAGGAGTCTCGTCCCACCTGAATCCTGCCGTGACGCTGGCCCAGGCGTCCGTGCGC
AAGTTTCCGATCGCCAAAGTGCCGCTATACTTCGCGGCTCAGTACCTGGGTGGCTTCGTC
GGTGCGGCGCTCGTGTTTGCCACCTACAAAGACGCTATTGAACACTTCGACCAGGGAATC
CGCCAAGTGACGGGAGAGAAGGCCACGGCTGGTATATTTGCAACTTACCCCAGACCACAC
GTCTCCACTCTGACCTGCTTCATTGATCAGGTCATCGCAACGGGCATAATGATGGTGTGC
GTCGAGGCCATCGGCGACACTCGCAACTTCGGCGGCATTCCGCCGCACATTCACCCAATC
TGCTTGGGTCTCATGATCATGGCTATTATCTTCAGTTTCGCCTACAACTGCATGTGCCTC
GAGTCTAGAGGGCCCTTCGAACAAAAACTCATCTCAGAAGAGGATCTGAATATGCATAC
CGGTCATCATCACCATCACCATTGA

Figure 3A
MAITSVITLSLLVVGALAGSKQDANNYIDTVLRDHLPANVRSLNLDPTHLPGFNFKVDSTG
PTNRDLKAQFPSGMLYGLSSVVRRRGDCGVPGWQGSSVTTGCYVSLDSLRLTFDGSVSGY
SLLGGKKNVSLDLVVEKTNAFVEATAPFGQQATLKTLTLSGIEFRVNVNKKLELNDKREK
KFLKAVRQSASNILLGIVNSSFREALSRSVSKVPLPSP*

Figure 3B
MAITSVITLSLLVVGALAGSKQDTNNYIDTVLRDHLPANVRSLNLDPTHLPGFNFKVDSTG
PTNRDLKAQFPSGMLYGLSSVVRRRGDCGVPGWQGSSVTTGCYVSLDSLRLTFDGSVSGY
SLLGGKKNVSLDLVVEKTNAFVEATAPFGQQATLKTLTLSGIEFRVNVNKKLELNDKREK
KFLKAVRQSASNILLGIVNSSFREALSRSVSKVPLPSPRPPAYVEQKLISEEDLNSAVDHHH
HHH*

Figure 3C
MAITSVITLSLLVVGALAGSKQDTNNYIDTVLRDHLPANVRSLNLDPTHLPGFNFKVDSTG
PTNRDLKAQFPSGMLYGLSSVVRRRGDCGVPGWQGSSVTTGCYVSLDSLRLTFDGSVSGY
SLLGGKKNVSLDLVVEKTNAFVEATAPFGQQATLKTLTLSGIEFRVNVNKKLELNDKREK
KFLKAVRQSASNILLGIVNSSFREALSRSVSKVPLPSPRPPAYVEQKLISEEDLNSAVDHHH
HHH*

Figure 4A

AAGCAGTGGTATCAACGCAGAGTACGCGGGGACAGAGCTCGGGGAAGACGCCGTGAAAG
GTTGCTGCACAAA<u>ATGGCCATCACTTCTGTAATCACCTTGAGTCTGCTTGTCGTCGGCGC</u>
<u>ACTCGCTGGCTCCAAGCAGGATGCCAACAACTACATCGACACGGTGCTTCGCGACCACCT</u>
<u>AGCGGCCAACGTGCGTTCGCTCAACCTGGACCCGACTCACTTGCCGGGTTTCAACTTCAA</u>
<u>GGTCGACTCGACTGGCCCGACCAACCGGGACCTGAAGGCGCAGTTCCCTTCGGGCATGCT</u>
<u>GTACGGCCTGTCGAGCGTGGTGCGCCGTCGCGGCGACTGCGGCGTACCGGGCTGGCAGGG</u>
<u>CTCGAGCGTCACCACTGGCTGCTACGTGTCCCTCGACTCGCTGCGACTCACCTTCGACGGA</u>
<u>AGCGTAAGCGGCTACAGCCTTCTCGGTGGCAAAAAGAACGTCAGCCTCGACCTGGTCGTC</u>
<u>GAGAAGACCAATGCCTTCGTTGAGGCCACGGCACCCTTCGGTCAGCAAGCGACGCTGAAG</u>
<u>ACGCTCACCTTGAGCGGCATCGAGTTCCGCGTGAACGTGAACAAGAAGCTCGAATTGAAC</u>
<u>GACAAGCGCGAGAAGAAGTTCCTCAAGGCCGTCAGGCAGTCGGCGAGCAACATCCTTCTG</u>
<u>GGCATCGTGAACTCATCCTTCCGCGAGGCTCTCAGCCGCTCCGTGAGCAAGGTGCCACTG</u>
<u>CCCAGTCCATGAAAAAAAAAAAAAAAAAAAAAAAAAAAAAAAACCCAAGGAGAAATACG</u>
AACAACGACGAATTGAAATAAACGACGAAACGTGCTGCAATGCATCA

Figure 4B

<u>ATGGCCATCACTTCTGTAATCACCTTGAGTCTGCTTGTCGTCGGTGCACTCGCTGGCTCC</u>
<u>AAGCAGGATACCAACAACTACATCGACACGGTGCTTCGCGACCACCTACCGGCCAACGTG</u>
<u>CGTTCGCTCAACCTGGACCCGACTCACTTGCCGGGTTTCAACTTCAAGGTCGACTCGACT</u>
<u>GGTCCGACCAACCGGGACCTGAAGGCGCAGTTCCCTTCGGGCATGCTGTACGGCCTGTCG</u>
<u>AGCGTGGTGCGCCGTCGCGGCGATTGCGGCGTTCCGGGCTGGCAGGGCTCGAGCGTCACC</u>
<u>ACTGGCTGCTACGTGTCCCTCGACTCGCTGCGACTCACCTTCGACGGAAGCGTAAGCGGC</u>
<u>TACAGCCTTCTCGGTGGCAAAAAGAACGTCAGCCTCGACCTGGTCGTCGAGAAGACCAAT</u>
<u>GCCTTCGTTGAGGCCACGGCACCCTTCGGTCAGCAAGCGACGCTGAAGACGCTCACCTTG</u>
<u>AGCGGCATCGAGTTCCGCGTGAACGTGAACAAGAAGCTCGAATTGAACGACAAGCGCGA</u>
<u>GAAGAAGTTCCTCAAGGCCGTCAGGCAGTCGGCGAGCAACATCCTTCTGGGCATCGTGAA</u>
<u>CTCATCCTTCCGCGAGGCTCTCAGCCGCTCCGTGAGCAAGGTGCCACTGCCCAGTCCGCGG</u>
CCGCCAGCTTACGTAGAACAAAAACTCATCTCAGAAGAGGATCTGAATAGCGCCGTCGAC
CATCATCATCATCATCATTGA

Figure 4C

AAAATGGCCATCACTTCTGTAATCACCTTGAGTCTGCTTGTCGTCGGTGCACTCGCTGGC
TCCAAGCAGGATACCAACAACTACATCGACACGGTGCTTCGCGACCACCTACCGGCCAAC
GTGCGTTCGCTCAACCTGGACCCGACTCACTTGCCGGGTTTCAACTTCAAGGTCGACTCG
ACTGGTCCGACCAACCGGGACCTGAAGGCGCAGTTCCCTTCGGGCATGCTGTACGGCCTG
TCGAGCGTGGTGCGCCGTCGCGGCGATTGCGGCGTTCCGGGCTGGCAGGGCTCGAGCGTC
ACCACTGGCTGCTACGTGTCCCTCGACTCGCTGCGACTCACCTTCGACGGAAGCGTAAGC
GGCTACAGCCTTCTCGGTGGCAAAAAGAACGTCAGCCTCGACCTGGTCGTCGAGAAGACC
AATGCCTTCGTTGAGGCCACGGCACCCTTCGGTCAGCAAGCGACGCTGAAGACGCTCACC
TTGAGCGGCATCGAGTTCCGCGTGAACGTGAACAAGAAGCTCGAATTGAACGACAAGCG
CGAGAAGAAGTTCCTCAAGGCCGTCAGGCAGTCGGCGAGCAACATCCTTCTGGGCATCGT
GAACTCATCCTTCCGCGAGGCTCTCAGCCGCTCCGTGAGCAAGGTGCCACTGCCCAGTCC
TCGAGGTCACCCATTCGAACAAAAACTCATCTCAGAAGAGGATCTGAATATGCATACCGG
TCATCATCACCATCACCATTGA

Figure 5

ATGAAGATTGAGAACTTGTTGATTAGACAATTGATTAACGAGTTCTTGGGTACTATGAT
TTTGATTACTATTGGTGACTCTATTATGGCTATTATTATTGCTGGTGACAACGAGTCTTT
GGCTGCTTGCGTTGGTCCATTGGGTTGGGGTGTTGCTATTTACGTTGCTGTTCAAATTTC
TGGTGGTGTTTCTTCTCACTTGAATCCAGCTGTTACTTTGGCTCAAGCTTCTGTTAGAAA
GTTTCCAATTGCTAAAGTTCCATTGTACTTCGCTGCTCAATACTTGGGTGGTTTCGTTGG
TGCTGCTTTGGTTTTTGCTACTTACAAAGACGCTATTGAACACTTCGACCAAGGTATTAG
ACAAGTTACTGGTGAGAAGGCTACTGCTGGTATTTTTGCTACTTACCCAAGACCACACGT
TTCTACTTTGACTTGCTTCATTGATCAAGTTATTGCTACTGGTATTATGATGGTTTGCGT
TGAGGCTATTGGTGACACTAGAAACTTCGGTGGTATTCCACCACACATTCACCCAATTTG
CTTGGGTTTGATGATTATGGCTATTATTTTCTCTTTCGCTTACAACTGCATGTGCC

Figure 6

ATGGCTATTACTTCTGTTATTACTTTGTCTTTGTTGGTTGTTGGTGCTTTGGCTGGTTCT
AAGCAAGATGCTAACAACTACATTGACACTGTTTTGAGAGACCACTTGCCAGCTAACGTT
AGATCTTTGAACTTGGACCCAACTCACTTGCCAGGTTTCAACTTCAAGGTTGACTCTACT
GGTCCAACTAACAGAGACTTGAAGGCTCAATTCCCATCTGGTATGTTGTACGGTTTGTCT
TCTGTTGTTAGAAGAAGAGGTGACTGCGGTGTTCCAGGTTGGCAAGGTTCTTCTGTTACT
ACTGGTTGCTACGTTTCTTTGGACTCTTTGAGATTGACTTTCGACGGTTCTGTTTCTGGT
TACTCTTTGTTGGGTGGTAAAAAGAACGTTTCTTTGGACTTGGTTGTTGAGAAGACTAA
TGCTTTCGTTGAGGCTACTGCTCCATTCGGTCAACAAGCTACTTTGAAGACTTTGACTTT
GTCTGGTATTGAGTTCAGAGTTAACGTTAACAAGAAGTTGGAATTGAACGACAAGAGAG
AGAAGAAGTTCTTGAAGGCTGTTAGACAATCTGCTTCTAACATTTTGTTGGGTATTGTT
AACTCTTCTTTCAGAGAGGCTTTGTCTAGATCTGTTTCTAAGGTTCCATTGCCATCTCC

VACCINATION OF ANIMALS TO ELICIT A PROTECTIVE IMMUNE RESPONSE AGAINST TICK INFESTATIONS AND TICK-BORNE PATHOGEN TRANSMISSION

CROSS-REFERENCE TO RELATED APPLICATIONS

This application is a divisional patent application of and claims priority to U.S. patent application Ser. No. 13/479,486 filed on May 24, 2012 (now U.S. Pat. No. 8,722,063), the contents of which are incorporated herein by reference in its entirety.

BACKGROUND OF THE INVENTION

Field of the Invention

The invention relates to novel proteins and their genes from the cattle tick, Rhipicephalus microplus, and their use as vaccines to control and prevent tick infestations in treated livestock, including bovines, which protects them against the transmission of tick-borne pathogens.

Description of the Prior Art

The cattle tick (also referred to as the southern cattle tick), Rhipicephalus (Boophilus) microplus, was declared to be eradicated from the US by 1943 (Graham and Hourrigan, 1977. J. Med. Entomol. 13:629-658), and all cattle presented for importation at the Texas-Mexico border are treated with acaricides to prevent reintroduction. However, there is a risk of the reestablishment of this tick in the US due to the presence of acaricide-resistant populations in Mexico (Miller et al., 2005. J. Med. Entomol. 42:912-917). Rhipicephalus microplus is a vector for the protozoan agents causing cattle fever, Babesia bovis and Babesia bigemina. Since cattle fever is endemic in Mexico, and all imported cattle are checked only for ticks but not for infection with this parasite, there is a constant threat of the resumption of cattle fever transmission in the US. This threat has triggered the search for new, environmentally safe and effective techniques for control of R. microplus that can be integrated with conventional chemical control methods.

Anti-tick vaccines are a potential alternative to chemical control methods, but the tick-protective antigens identified thus far remain to be developed and marketed by private concerns for commercial use by livestock producers (de la Fuente and Kocan, 2006. Parasite Immunol. 28:275-283). Development of novel tick control strategies requires increased knowledge of the complement of proteins expressed in R. microplus. Three proteome studies have been published for R. microplus. Sequence information for 20 abundantly expressed larval proteins, representing multiple cuticular proteins, a cytoskeletal protein, a salivary gland-associated protein, several housekeeping proteins, and tropomyosin have been described (Untalan et al., 2005. Insect Biochem. Mol. Biol. 35:141-151). Nineteen membrane proteins were identified that were differentially expressed in the ovaries in uninfected and Babesia bovis-infected ticks. Ovarian proteins that were up-regulated in infected ticks included calreticulin, two myosin subunits, an endoplasmic reticulum protein, a peptidyl-prolyl cis-trans isomerase (PPIase), a cytochrome c oxidase subunit, a glutamine synthetase, and a family of Kunitz-type serine protease inhibitors. Among the down-regulated ovarian proteins were another PPIase, a hemoglobin subunit, and a lysozyme (Rachinsky et al., 2007. Insect Biochem. Mol. Biol. 37:1291-1308). More recently, Rachinsky et al. (2008. Vet. Parasit. 152:294-313) described an extensive survey of proteins in the midgut epithelium that were regulated in response to infection as part of an ongoing effort to establish a proteome database to be utilized to identify specific proteins that may be involved in successful pathogen transmission or tick feeding, and which could serve as candidates for tick control methods.

However, despite these and other advances, the need remains for improved techniques for control of the southern cattle tick.

SUMMARY OF THE INVENTION

We have now discovered immunogenic proteins of the cattle tick, Rhipicephalus microplus, and the genes encoding these proteins, which protect bovines and other livestock and effectively control cattle tick infestations. The immunogenic proteins isolated from the cattle tick include an aquaporin protein and a gut membrane protein (TC5777). Each of the proteins are also antigenic, eliciting a protective immune response in livestock, including bovines, to the cattle tick, and can be administered as vaccines. Alternatively, the isolated DNA sequences which encode these proteins can be incorporated into nucleic acid constructs, which could be utilized as DNA vaccines for eliciting a protective immune response in bovines and other livestock against the cattle tick. In this embodiment, the nucleic acid constructs are administered to a subject animal such that the proteins are expressed in vivo within the cells of the vaccinated animal. The nucleic acid constructs may also be used for the transformation of cells to produce recombinant proteins. Induction of the immune response significantly reduces or eliminates the infestation of the treated animals with the tick. Moreover, as the cattle tick is a vector for Babesia bovis and B. bigemina, the causative agents for cattle fever, the reduction in the incidence of cattle tick infestation afforded by the vaccines herein reduces the incidence of cattle fever in susceptible animals.

In accordance with this discovery, it is an object of this invention to provide novel protective vaccines against the cattle tick, R. microplus, in livestock, including bovines.

Another object of the invention is to provide novel protective vaccines that control and prevent infestations with the cattle tick, R. microplus, in livestock, including bovines.

A further object of the invention is to provide vaccines comprising immunogenic proteins that control and prevent infestations with the cattle tick, R. microplus, in livestock, including bovines.

Another object of the invention is to provide nucleic acid sequences encoding the immunogenic proteins of the cattle tick, R. microplus.

Yet another object of the invention is to provide vaccines comprising nucleic acid constructs encoding immunogenic proteins that control and prevent infestations with the cattle tick, R. microplus, in livestock, including bovines.

Still another object of the invention is to provide novel protective vaccines that control and prevent infestations with the cattle tick, R. microplus, in livestock, including bovines, and thereby reduce or eliminate the incidence of cattle fever caused by Babesia bovis and B. bigemina.

Other objects and advantages of this invention will become readily apparent from the ensuing description.

BRIEF DESCRIPTION OF THE DRAWINGS

FIG. 1A shows the amino acid sequence (SEQ ID NO: 1) of the fragment of the aquaporin protein, Contig 12018, described herein which was isolated from R. microplus. FIG.

1B shows the amino acid sequence (SEQ ID NO: 2) of the aquaporin protein fragment as cloned into and produced by *Pichia pastoris* expression vector pPICZalphaA as described in the Example. The amino acids of the tick aquaporin protein are underlined (amino acids 92-290 of SEQ ID NO: 2), while extra amino acids not of tick origin but from the vector are not underlined (amino acids 1-91 and 291-317 of SEQ ID NO: 2). FIG. 1C shows the amino acid sequence (SEQ ID NO: 3) of the aquaporin protein fragment as cloned into and produced by the DNA vaccine expression vector pcDNA4mycHis C as described in the Example. The amino acids of the tick aquaporin protein are underlined (amino acids 1 and 3-198 of SEQ ID NO: 3), while substituted/extra amino acids not of tick origin are not underlined (amino acids 2 and 199-226 of SEQ ID NO: 3). Although the substituted/extra amino acids are not of tick origin, they are present in the structure of the final protein product used in the vaccine in the Example.

FIG. 2A shows the nucleotide sequence (SEQ ID NO: 5) of the cDNA from *R. microplus* encoding the isolated aquaporin protein fragment of FIG. 1A and includes an untranslated 5' region. The translated region coding for the isolated aquaporin protein fragment of FIG. 1A is underlined and corresponds to nucleotides 348-947 of the sequence. FIG. 2B shows the aquaporin nucleotide sequence (SEQ ID NO: 6) as cloned into *P. pastoris* expression vector pPICZalphaA as described in the Example. The underlined sequence (nucleotides 274-870) corresponds to the nucleotide sequence of the coding region of FIG. 2A above except that the three 3' terminal nucleotides have been removed. The nucleotide sequence shown includes extra, optional vector-provided nucleotides (nucleotides 1-273 and 871-954, not underlined) which code for the extra amino acids not of tick origin. FIG. 2C shows the aquaporin nucleotide sequence (SEQ ID NO: 7) as cloned into the DNA expression vector pcDNA4mycHis C as described in the Example. The underlined sequence (nucleotides 4-598) corresponds to the nucleotide sequence of the coding region of FIG. 2A above except that the second codon triplet has been changed from AAG to GAG, and the five 3' terminal nucleotides have been removed. The nucleotide sequence shown includes extra, optional DNA vaccine expression vector-provided nucleotides (1-3 and 599-684, not underlined) of which the 5' terminal nucleotides code for the extra amino acids not of tick origin. The nucleotide sequence corresponding to nucleotides 4-598 of SEQ ID NO: 7 is also presented as SEQ ID NO: 8 (wherein the extra nucleotides from the DNA vaccine expression vector are not included).

FIG. 3A shows the amino acid sequence (SEQ ID NO: 9) of the tick gut membrane protein TC5777 of this invention which is isolated from and unique to *R. microplus*. FIG. 3B shows the amino acid sequence (SEQ ID NO: 10) of the TC5777 protein as cloned into and produced by *P. pastoris* expression vector pPICZ C as described in the Example. The amino acids of the TC5777 protein are underlined (amino acids 1-219 of SEQ ID NO: 10), while the extra amino acids not of tick origin are not underlined (amino acids 220-246 of SEQ ID NO: 10). FIG. 3C shows the amino acid sequence (SEQ ID NO: 11) of the TC5777 protein as cloned into and produced by the DNA vaccine expression vector pcDNA4mycHis C as described in the Example. The amino acids of the TC5777 protein are underlined (amino acids 1-219 of SEQ ID NO: 11), while the extra amino acids not of tick origin are not underlined (amino acids 220-246 of SEQ ID NO: 11). Although the extra amino acids are not of tick origin, they are present in the structure of the final protein product used in the vaccine in the Example.

FIG. 4A shows the nucleotide sequence (SEQ ID NO: 12) of the cDNA from *R. microplus* encoding the isolated tick gut membrane protein TC5777 of FIG. 3A and includes untranslated 5' and 3' regions. The translated region coding for the isolated TC5777 protein of FIG. 3A is underlined and corresponds to nucleotides 73-728 of the sequence. FIG. 4B shows the TC5777 nucleotide sequence (SEQ ID NO: 13) as cloned into *P. pastoris* expression vector pPICZ C as described in the Example. The underlined sequence (nucleotides 1-656) corresponds to the nucleotide sequence of the coding region of FIG. 4A above. The nucleotide sequence shown includes extra, optional vector-provided nucleotides (nucleotides 657-741, not underlined) which code for the extra amino acids not of tick origin. FIG. 4C shows the TC5777 nucleotide sequence (SEQ ID NO: 14) as cloned into the DNA expression vector pcDNA4mycHis C as described in the Example. The underlined sequence (nucleotides 4-659) corresponds to the nucleotide sequence of the coding region of FIG. 4A above. The nucleotide sequence shown includes extra, optional DNA vaccine expression vector-provided nucleotides (1-3 and 660-741, not underlined) which code for the extra amino acids not of tick origin.

FIG. 5 shows a nucleotide sequence (SEQ ID NO: 15) encoding the isolated aquaporin protein fragment of FIG. 1A wherein the translated or coding region of the nucleotide sequence of FIG. 2A (nucleotides 348-942) has been optimized to enhance translation in *P. pastoris*.

FIG. 6 shows a nucleotide sequence (SEQ ID NO: 16) encoding the isolated TC5777 protein of FIG. 3A wherein the translated or coding region of the nucleotide sequence of FIG. 4A (nucleotides 73-728) has been optimized to enhance translation in *P. pastoris*.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as it occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in viva when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Stringent Hybridization Conditions. The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will differ in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent hybridization conditions comprise hybridization in 50% formamide, 1 M NaCl, 1% SDS at 42° C., and a wash in 0.1×SSC at 60 to 65° C. It is also understood that due to the advances in DNA PCR and sequencing approaches that issues of gene identity and homology may be determined by sequence based rather than hybridization approaches.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

Transcription. The process of producing mRNA from a structural gene.

Translation. The process of producing a polypeptide from mRNA.

Vaccine. Vaccine is defined herein in its broad sense to refer to any type of biological agent in an administrable form capable of stimulating a protective immune response in an animal inoculated with the vaccine. For purposes of this invention, the vaccine may comprise either one or more of the immunogenic (antigenic) proteins or nucleic acid constructs encoding these proteins.

DETAILED DESCRIPTION OF THE INVENTION

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

We have isolated two immunogenic proteins from the cattle tick, an aguaporin protein fragment and a tick gut membrane protein, TC5777, which can be effectively used as protective vaccines against the cattle tick, *Rhipicephalus microplus* in livestock, including bovines. Moreover, while we have demonstrated efficacy using aquaporin protein fragments, it is recognized that larger fragments of the protein which encompass the disclosed fragments, or the entire aguaporin protein, may also be used herein. This aquaporin protein is believed to play a role in the osmo-regulation system of the tick, while the TC5777 is a gut membrane protein of the tick which is up-regulated in response to infection of the tick gut by *B. bovis*. The proteins have been isolated, substantially free from other proteins or cell components which are normally present in the cells of the tick, such that the aquaporin or TC5777 proteins are the only significant protein or peptide in the sample and may be used effectively as a vaccine. Moreover, both of the proteins have been produced in recombinant form as described herein below. The term "isolated" encompasses not only proteins which have been recovered from naturally occurring cells, but also recombinant proteins and synthesized proteins. Each of the aquaporin protein fragments and TC5777 gut membrane protein, including recombinants, are immunogenic, effective for eliciting a protective immune response against the cattle tick, which response is mediated by humoral, i.e., antibodies, and/or cellular processes. The gut membrane (i.e., TC5777) protein of *R. microplus* has been previously described by Rachinsky et al. (2008, ibid) as being up-regulated in response to infection with the *B. bovis* parasite, and a partial amino acid sequence was provided. However, the function of the TC5777 gut membrane protein, its use as a vaccine and its gene, have not been described.

The isolated aquaporin protein fragment and TC5777 gut membrane protein of *R. microplus* have been sequenced, and their amino acid sequences are shown in FIGS. 1A and 3A, respectively. The amino acid sequence of the isolated aquaporin protein fragment corresponds to SEQ ID NO: 1, while the amino acid sequence of the TC5777 gut membrane protein corresponds to SEQ ID NO: 9. The isolated aquaporin protein fragment has a calculated molecular weight of 21.2 kDa based on the amino acid sequence. The isolated TC5777 gut membrane protein has a calculated molecular weight of 23.5 kDa based on the amino acid sequence and an observed molecular weight of approximately 24 kDa as determined by SDS-polyacrylamide gel electrophoresis. Moreover, when utilizing recombinant proteins, the aquaporin protein fragment may be modified to assist cloning in the selected vector, and the expressed proteins (aquaporin or TC5777) may further include optional, additional terminal amino acid sequences from the vector (not of tick origin). For example, FIG. 1B shows the amino acid sequence (SEQ ID NO: 2) of the aquaporin protein fragment as cloned into and produced by the *Pichia pastoris* expression vector pPICZalphaA as described in the Example. The underlined sequence of FIG. 1B corresponds to the amino acid sequence of FIG. 1A, except that the C-terminal amino acid (L) of the isolated fragment has been removed to assist cloning of the aquaporin gene into the plasmid. The amino acid sequence also includes extra, optional amino acids from the cloning vector. The amino acids of the tick aquaporin protein are underlined (amino acids 92-290 of SEQ ID NO: 2), while the extra amino acids not of tick origin are not underlined (amino acids 1-91 and 291-317 of SEQ ID NO: 2). FIG. 1C shows the amino acid sequence (SEQ ID NO: 3) of the aquaporin protein fragment as cloned into and produced by the DNA vaccine expression vector pcDNA4mycHis C also as described in the Example. The underlined sequence corresponds to the amino acid sequence of FIG. 1A above, except that amino acid 2 has been changed (from K to E) and the two C-terminal amino acids (PL) of the isolated fragment have been removed to assist cloning of the aquaporin gene into the plasmid. Thus, amino acids 3-198 of SEQ ID NO: 1 are common to each of the aquaporin sequences of FIGS. 1A, B and C. The amino acid sequence of FIG. 1C also includes optional amino acids from the DNA vaccine expression vector. The amino acids of the tick aquaporin protein are underlined (amino acids 1 and 3-198 of SEQ ID NO: 3), while the changed/extra amino acids not of tick origin are not underlined (amino acids 2 and 199-226 of SEQ ID NO: 2). The amino acid sequence corresponding solely to amino acids 1-198 of SEQ ID NO: 3 is also presented as SEQ ID NO: 4 (the extra amino acids from the DNA vaccine expression vector are not included). Similarly, FIG. 3B shows the amino acid sequence (SEQ ID NO: 10) of the TC5777 protein as cloned into and produced by the *P. pastoris* expression vector pPICZ C as described in the Example. The underlined sequence in FIG. 3B corresponds to the amino acid sequence of FIG. 3A (i.e., the amino acid sequence of the TC5777 protein), and the non-underlined amino acids correspond to the optional amino acids from the vector. Thus, the amino acids of the TC5777 protein correspond to amino acids 1-219 of SEQ ID NO: 10, while the extra amino acids not of tick origin correspond to amino acids 220-246 of SEQ ID NO: 10. FIG. 3C shows the amino acid sequence (SEQ ID NO: 11) of the TC5777 protein as cloned into and produced by the DNA vaccine expression vector pcDNA4mycHis C. Again, the underlined sequence in FIG. 3C corresponds to the amino acid sequence of FIG. 3A above. The amino acid sequence shown includes extra, optional amino acids from the DNA vaccine expression vector. The amino acids of the TC5777 protein are underlined (amino acids 1-219 of SEQ ID NO: 11), while the extra amino acids not of tick origin are not underlined (amino acids 220-246 of SEQ ID NO: 11).

It is envisioned that the *R. microplus* aquaporin and TC5777 gut membrane proteins may be synthesized by any suitable method well known to those skilled in the art of peptide synthesis, such as exclusively solid-phase techniques, partial solid-phase techniques, fragment condensation, or classical solution addition. For example, without being limited thereto, suitable solution phase synthesis methods are described by Finn and Hoffman [In "Proteins," Vol. 2, 3rd Ed., H. Neurath and R. L. Hill (eds.), Academic Press, New York, pp. 105-253 (1976)], while solid phase synthesis methods are described by Barany and Merrifield [In "The Peptides," Vol. 2, E. Gross and J. Meienhofer (eds.), Academic Press, New York, pp. 3-284 (1979)], and stepwise solid phase synthesis methods are described by Merrifield [J. Am. Chem. Soc. 85: 2149-2154 (1963)], the contents of each of which are incorporated herein by reference. However, the proteins are preferably produced by recombinant DNA techniques which are particularly suitable for large-scale use. Without being limited thereto, nucleotide sequences encoding the proteins which are preferred for use in recombinant DNA techniques are described in detail below. The synthetic proteins may be obtained by transforming a microorganism using an expression vector including a promoter or operator, or both, together with one or both of the aquaporin and TC5777 gut membrane structural genes and causing such transformed microorganisms to express the proteins.

The genes encoding each of the aquaporin protein fragment and TC5777 gut membrane protein of *R. microplus* have also been isolated and their cDNA nucleic acid sequences are shown in FIGS. 2A and 4A, respectively. The nucleic acid sequence of the translated region of the cDNA encoding the aquaporin protein fragment corresponds to nucleotides 348-947 of SEQ ID NO: 5, while the nucleic acid sequence of the translated region of the cDNA encoding the TC5777 gut membrane protein corresponds to nucleotides 73-728 of SEQ ID NO: 12. FIG. 2A also includes an untranslated 5' region (not underlined), while FIG. 4A includes untranslated 5' and 3' regions (not underlined). As used herein, isolated nucleic acid sequences refer to sequences which have been substantially separated from other nucleic acids or cell components which are normally present in the cells of the tick, such that the aquaporin or TC5777 gut membrane encoding sequences are the only significant sequences in the sample that can be used to express or produce the proteins in a host cell as described below. The term encompasses not only nucleic acid sequences which have been recovered from naturally occurring cells, but also recombinant or cloned nucleic acid sequences, and synthesized nucleic acid sequences. The nucleic acid sequences may be recovered from cells of *R. microplus*, for example, by constructing a genomic DNA or cDNA library and screening for the aquaporin or TC5777 gut membrane protein nucleic acid using the disclosed sequences as probes. However, in a preferred embodiment, the sequences are synthesized using techniques established in the art for automated DNA synthesis or amplification. As used herein, the nucleic acid sequences of the aquaporin and TC5777 gut membrane proteins encompass either or both of the coding strand or its complement.

As noted above, the amino acid sequence of the aquaporin protein fragment may be modified to assist cloning in the selected vector, and either of the expressed proteins (aquaporin or TC5777) may further include optional, additional terminal amino acid sequences from the vector (not of tick origin). Thus, the nucleic acid sequences may be modified to reflect these changes. For example, FIG. 2B shows the aquaporin nucleotide sequence (SEQ ID NO: 6) as cloned into the *P. pastoris* expression vector pPICZalphaA as described in the Example. The underlined sequence of FIG. 2B (nucleotides 274-870) corresponds to the nucleotide sequence of the coding region of FIG. 2A above except that the three 3' terminal nucleotides (nucleotides 945-947 of FIG. 2A) have been removed to assist cloning of the gene into the plasmid. The nucleotide sequence shown includes extra, optional vector-provided nucleotides (nucleotides 1-273 and 871-954, not underlined) which code for the extra amino acids not of tick origin (amino acids 1-91 and 291-317 of SEQ ID NO: 2). FIG. 2C shows the aquaporin nucleotide sequence (SEQ ID NO: 7) as cloned into the DNA expression vector pcDNA4mycHis C as described in the Example. The underlined sequence (nucleotides 4-598) corresponds to the nucleotide sequence of the coding region of FIG. 2A above except that the second codon triplet (nucleotides 351-353 of FIG. 2A) has been changed from AAG to GAG, and the five 3' terminal nucleotides (nucleotides 943-947 of FIG. 2A) have been removed, to assist cloning of the gene into the plasmid and enhance translation. Thus, nucleotides 354-942 of SEQ ID NO:5 are common to each of the aquaporin coding sequences of FIGS. 2A, B and C. The nucleotide sequence shown includes extra, optional DNA vaccine expression vector-provided nucleotides on both of the 3' and 5' ends (1-3 and 599-684, not underlined) of which the 3' terminal nucleotides code for the extra amino acids not of tick origin (amino acids 200-226 of SEQ ID NO: 2). The nucleotide sequence corresponding to nucleotides 4-598 of SEQ ID NO: 7 is also presented as SEQ ID NO: 8 (wherein the extra nucleotides from the DNA vaccine expression vector are not included). Similarly, FIG. 4B shows the TC5777 nucleotide sequence (SEQ ID NO: 13) as cloned into *P. pastoris* expression vector pPICZ C as described in the Example. The underlined sequence (nucleotides 1-656) corresponds to the nucleotide sequence of the coding region of FIG. 4A above. The nucleotide sequence shown includes extra, optional vector-provided nucleotides (nucleotides 657-741, not underlined) which code for the extra amino acids not of tick origin (amino acids 220-246 of SEQ ID NO: 10). FIG. 4C shows the TC5777 nucleotide sequence (SEQ ID NO: 14) as cloned into the DNA expression vector pcDNA4mycHis C as described in the Example. The underlined sequence (nucleotides 4-659) corresponds to the nucleotide sequence of the coding region of FIG. 4A above. The nucleotide sequence shown includes extra, optional DNA vaccine expression vector-provided nucleotides (1-3 and 660-741, not underlined) which code for the extra amino acids not of tick origin (amino acids 220-246 of SEQ ID NO: 11). In addition, because of the degeneracy of the genetic code, there exists a finite set of nucleotide sequences which can code for a given amino acid sequence. Consequently, nucleic acids may be identical in sequence to the sequence which is naturally occurring or they may include alternative codons which encode the same amino acid as that which is found in the naturally occurring sequence. Furthermore, nucleic acids may include codons which represent conservative substitutions of amino acids as are well known in the art. Moreover, because of the degeneracy of the genetic code, different species can preferentially use different codons to code for the same amino acid and significant differences in tRNA abundance can exist. Translation of recombinant proteins can often be enhanced by optimizing codon usage to the preferred codons used by the expression species. For example, in the yeast *P. pastoris* the amino acid arginine is encoded by the nucleotide triplet of AGA approximately 10 times more frequently than by the nucleotide triplet of CGG. Substitution of CGG triplets with AGA in a *R. microplus* protein coding region used in a recombinant *P. pastoris* expression system would be expected to enhance recombinant protein expression levels. It is understood that all such equivalent sequences are operable variants of the disclosed sequences, since all give rise to the same aquaporin or TC5777 gut membrane proteins (i.e., the same amino acid sequence) during in vivo transcription and translation, and are hence encompassed herein. Without being limited thereto, examples of codon-optimized sequences which would be suitable for enhancing translation of the aquaporin protein fragment and TC5777 gut membrane protein in *P. pastoris* are shown in FIGS. 5 and 6, respectively. The sequence of FIG. 5 (SEQ ID NO: 15) corresponds to the translated or coding region of the nucleotide sequence of FIG. 2A (nucleotides 348-942) which has been optimized to enhance translation in *P. pastoris*. The sequence of FIG. 6 (SEQ ID NO: 16) corresponds to the translated or coding region of the nucleotide sequence of FIG. 4A (nucleotides 73-728) which has been optimized to enhance translation in *P. pastoris*. DNA sequences which contain significant sequence similarity to the coding regions of the nucleotide sequence of SEQ ID NOs: 5 and 12 are also encompassed by the invention. As defined herein, two DNA sequences contain significant sequence similarity when at least 85% (preferably at least 90% and most preferably 95%) of the nucleotides match over the defined length of the sequence. Sequences that are significantly similar can be identified in a Southern hybridization experiment under stringent hybridization conditions as is known in the art. See, for example, Sambrook et al., Molecular Cloning: A Laboratory Manual ($2^{nd}$ Ed.), Vol. 1-3, Cold Spring Harbor Laboratory, Cold Spring Harbor, N.Y., 1989, or DNA Cloning: A Practical Approach, Vol. I and II (Ed. D. N. Glover), IRL Press, Oxford, 1985.

Any one or combinations of the isolated cDNA nucleic acid sequences encoding the *R. microplus* aquaporin and TC5777 gut membrane proteins may be cloned into any suitable vector for subsequent use as either a DNA vaccine or for the production of recombinant *R. microplus* aquaporin or TC5777 gut membrane proteins. For use as a DNA vaccine, the nucleic acid constructs comprising the nucleic acid sequences encoding the *R. microplus* aquaporin and/or TC5777 gut membrane proteins are administered to a subject animal such that the proteins are expressed in vivo within the cells of the vaccinated animal. Similarly, where the object is the production of recombinant proteins, the nucleic acid constructs are used for the transformation of a microorganism and causing such transformed microorganism to express the proteins in vitro.

A variety of vectors are suitable for use herein, and are selected to be operable as cloning vectors or expression vectors in the selected host cell, although expression vectors are preferred. Numerous vectors are known to practitioners skilled in the art, and selection of an appropriate vector and host cell is a matter of choice. The vectors may, for example, be bacteriophage, plasmids (including linearized or circular plasmids), viruses or hybrids thereof, such as those described in Sambrook et al. (ibid) or Ausubel et al. (Current Protocols in Molecular Biology, John Wiley & Sons, Inc, 1995, the contents of each of which are herein incorporated by reference. Further, the vectors may be non-fusion vectors (i.e., those producing the proteins of the invention not fused to any heterologous polypeptide), or alternatively, fusion vectors (i.e., those producing the proteins fused to a vector encoded polypeptide). The fusion proteins would of course vary with the particular vector chosen. In accordance with a preferred embodiment, and particularly for applications as DNA vaccines, the vectors are eukaryotic expression vectors, most preferably plasmids. Particularly preferred plasmids for use herein include plasmids commercially available from Invitrogen Inc., Carlsbad, Calif. for both the DNA vaccine and recombinant protein vaccine protocols. The pcDNA 4/myc 5.1 kb vectors are designed for overproduction of recombinant proteins in mammalian cells. This plasmid contains a human cytomegalovirus immediate-early (CMV) promoter for high-level expression, a c-myc epitope and 6×His metal-binding peptide tag for facilitating protein purification and verification, and a Zeocin antibiotic resistance marker gene coding region for selection purposes. The preferred plasmids used to produce recombinant proteins are the pPICZ and pPICZα from Invitrogen Inc. Both plasmids contain the AOX1 gene promoter for methanol-inducible high-level expression in *Pichia pastoris*, a c-myc epitope and 6×His metal-binding peptide tag for facilitating protein purification and verification, and a Zeocin antibiotic resistance marker gene coding region for selection purposes. The pPICZα also contains a native *Saccharomyces cerevisiae* α-factor secretion signal.

Regardless of the specific vector utilized, various sites may be selected for insertion of the isolated nucleotide sequences. These sites are usually designated by the restriction enzyme or endonuclease that cuts them.

The particular site chosen for insertion of the selected nucleotide sequences into the vector to form a recombinant vector is determined by a variety of factors. These include size and structure of the protein to be expressed, susceptibility of the desired protein to enzymatic degradation by the host cell components and contamination by its proteins, expression characteristics such as the location of start and stop codons, and other factors recognized by those skilled in the art. None of these factors alone absolutely controls the choice of insertion site for a particular polypeptide. Rather, the site chosen reflects a balance of these factors, and not all sites may be equally effective for a given protein.

The nucleotide sequences comprising the *R. microplus* aquaporin protein fragment and/or TC5777 gut membrane protein encoding genes may be inserted into the desired vector by known techniques. If, however, the vector is to serve as an expression vector, the vector should have a promoter effective for expression in the selected host cell, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eukaryotic). Alternatively, any or all of the above control sequences may be ligated to the coding sequence prior to insertion into the vector.

For use in animal vaccinations, the isolated *R. microplus* aquaporin protein fragment and/or TC5777 gut membrane protein or the nucleic acid constructs comprising the nucleic acid sequences encoding these proteins, will typically be formulated in conjunction with a suitable pharmaceutically acceptable carrier or diluent as is known in the art, including, but not limited to, physiological saline, mineral oil, vegetable oils, aqueous carboxymethyl cellulose or polyvinylpyrrolidone. The skilled practitioner will recognize that such carriers should of course be compatible with the proteins or nucleic acid constructs. Phosphate buffered saline (PBS) is preferred. The concentration and amount of the proteins or nucleic acid constructs in the final composition may vary depending upon the desired use and type of response needed, and the host animal. In any event, the proteins or nucleic acid constructs should be provided in an amount effective to induce the preferred response as determined by routine testing. Appropriate adjuvants as known in the art may also be included in the formulation. Without being limited thereto, suitable adjuvants include but are not limited to mineral oil, vegetable oils, alum, Freund's incomplete adjuvant, and microparticles or nanoparticles or beads of biocompatible matrix materials such as (although not limited to) agar or polyacrylate. Other known immunogenic agents used in conventional vaccines for bovine may also be included in the formulation.

The immunogenic *R. microplus* aquaporin protein fragment and/or TC5777 gut membrane protein or the nucleic acid constructs comprising the nucleic acid sequences encoding these proteins are administered in an amount effective to reduce or eliminate the incidence of infestation of treated livestock, including bovines, with the cattle tick, *R. microplus*. As noted hereinabove, the administration of the *R. microplus* aquaporin and/or TC5777 gut membrane protein, or the nucleic acid constructs comprising the nucleic acid sequences encoding these proteins (such that the nucleic acid sequences are expressed and the encoded proteins are produced in vivo in the cells of the vaccinated animal), stimulates an immune response in the animal. Thus, as used herein, an "effective amount" of *R. microplus* aquaporin and/or TC5777 gut membrane protein or the nucleic acid constructs comprising the nucleic acid sequences encoding these proteins, is preferably defined as that amount which will elicit a protective immune response against the cattle tick, which may be either or both of antibody production against the protein(s) or a cell-mediated immune response against the tick, in a treated animal in comparison to an untreated control animal. In a preferred embodiment, an immune response may be demonstrated by production of antibodies against either or both of the *R. microplus* aquaporin and/or TC5777 gut membrane proteins, by a significant reduction in the percentage of animals infested with the cattle tick, by a significant reduction in the average number of cattle ticks on animals, or by a significant reduction in the number of viable eggs produced by the cattle ticks present on animals, all in vaccinated animals as compared to an unvaccinated control group (measured at a confidence level of at least 80%, preferably measured at a confidence level of 95%). The actual effective amount will of course vary with the specific vaccine component (protein vaccine or DNA vaccine), the age and size of the target animal, and the route of administration, and may be readily determined empirically by the practitioner skilled in the art using an antigen dose response assay. By way of example and without being limited thereto, for vaccines administered to bovine by subcutaneous or intramuscular injection, or with a needle-less device, it is envisioned that typical doses of protein vaccine (*R. microplus* aquaporin and/or TC5777 gut membrane proteins), may be greater than 10 μg protein/animal/dose, preferably between about 50 to 150 μg protein/animal/dose, while typical doses of DNA vaccine (nucleic acid constructs) may be greater than 100 μg of DNA construct/animal/dose, preferably between about 300 to 800 μg DNA construct/animal/dose.

The vaccines (*R. microplus* aquaporin and/or TC5777 gut membrane protein or the nucleic acid constructs comprising the nucleic acid sequences encoding these proteins) may be used for the treatment of livestock, including horses, sheep, and bovines such as dairy cows and preferably cattle. The vaccines may be effectively administered any time after the animal attains immunocompetence. The vaccines may be administered to the subject animal by any convenient route which enables an immune response. However, parenteral injection (e.g., subcutaneous, intravenous, or intramuscular) is preferred, with intradermal injection being particularly preferred for administration of the DNA vaccines and intramuscular injection being particularly preferred for administration of the protein vaccines. The vaccine products could also be administered using a needle-less device. The vaccine may be administered in a single dose or in a plurality of doses. Dependent upon rearing conditions, the vaccine may be administered in multiple doses, the timing of which may be readily determined by the skilled artisan.

Where the nucleic acid constructs are to be employed for the production of recombinant *R. microplus* aquaporin or TC5777 gut membrane proteins, a variety of vector-host cell expression systems may be employed. Strains of yeast, particularly *Pichia pastoris*, are preferred. However, the novel invention described here can be applied with numerous host cells that would desirable. Host strains may be of bacterial, fungal, insect cell line, plant, or yeast origin. Ascertaining the most appropriate host-vector system is within the skill of the person in the art.

DNA constructs may be introduced into the appropriate host cell by numerous methods described in the technical and scientific literature. Transformation of bacteria or yeast may be performed using standard techniques described in Sambrook et al., (ibid). Techniques for transforming filamentous fungi may include those described by Goosen et al. [Handbook for Applied Mycology, Arora, Elander & Mukerji, eds. (1992) pp. 151-195] and May et al. [Applied Molecular Genetics of Filamentous Fungi, Kinghorn and Turner, eds. (1992) pp. 1-27]. In general, linear or circular DNA constructs may be introduced into the host cell by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed host cell. These may include nutritional selection related to substrate utilization (such as, growth on acetamide containing medium) or prototrophy of a required growth product (such as, arginine, leucine, or uracil). Dominant selectable markers (such as, resistance to ampicillin, G418, hygromycin, and phleomycin) are also useful in selecting transformants that have taken up the introduced DNA construct.

The DNA construct may be replicated autonomously or integrated into the genome of the host cell. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

The following example is intended only to further illustrate the invention and is not intended to limit the scope of the invention which is defined by the claims.

EXAMPLE 1

Material and Methods

Ticks

Tick larvae used in this study to infest cattle for the cattle vaccine trials were obtained from a laboratory colony maintained at EMBRAPA Beef Cattle. The colony was established with *R. microplus* ticks collected from infested cattle in Campo Grande, MS, Brazil (Casquero-Cunha et al. In press). Fully engorged adult female ticks were collected upon host detachment and brought to the laboratory to allow oviposition. Egg masses were incubated in humidity chambers at 28° C. and 95% relative humidity to facilitate hatching. Larvae were used for infestation at 18 days after hatching. Nucleic acids were obtained from engorged adult female *Rhipicephalus (Boophilus) microplus* of the f20 La Minita strain maintained at The University of Idaho Holm Research Center (Moscow, Id.). The La Minita strain was originally collected in 1996 during an outbreak in Starr County, Texas and propagated at the USDA-ARS Cattle Fever Tick Research Laboratory in Edinberg, Tex. (Guerrero et al. 2001. J. Med. Entomol. 38:44-50).

RNA Purification

Total RNA was isolated using the FastPrep-24 Tissue and Cell Homogenizer and Lysing Matrix D (Qbiogene, Irvine, Calif., USA) as described in Saldivar of al. [2008. Microanalysis of acaricide-induced gene expression in the southern cattle tick, *Rhipicephalus (Boophilus) microplus*. Insect Mol Biol. 17:597-606] from gut tissue dissected from engorged adult female *Rhipicephalus (Boophilus) microplus*. The total RNA was DNAse treated following manufacturer's protocol using Turbo DNA-free kit (Ambion, Austin, Tex., USA).

cDNA Synthesis & RACE

One microgram DNase-free total RNA was used to make 5' and 3' cDNA using the SMART RACE cDNA Amplification Kit (Clontech Laboratories Inc., Mountain View, Calif., USA) and Superscript III Reverse Transcriptase (Life Technologies, Grand Island, N.Y., USA). Primers (Sigma-Aldrich, The Woodlands, Tex., USA) were designed from the target antigen sequences, synthesized, and used to obtain complete open reading frame sequences of each target antigen.

The Aquaporin target 5' end was obtained using 20 µL PCR reactions using 5' SMART RACE cDNA, ADVANTAGE 2 PCR Enzyme System (Clontech Laboratories Inc., Mountain View, Calif., USA), Universal Primer A and gene specific primer KB-126 according to manufacturer's protocol using the touchdown cycling profile suggested in the SMART RACE protocol booklet. This amplification product was used for a nested PCR using Nested Universal Primer A and gene specific primer KB-126 following manufacturer's protocol using a cycling profile of thirty cycles including a denaturing step of 94° C. for 30 sec, annealing step of 72° C. for 30 sec and extension step of 72° C. for 3 min.

The TC5777 gut membrane protein target 5' end was obtained similarly except gene specific primer KB-130 was used. The 3' end was obtained using the same conditions as the 5' RACE experiment with the exception of using 3' SMART RACE cDNA and gene specific primer KB-127 for primary PCR and primer KB-128 for the nested PCR.

The nested PCR products were analyzed using electrophoresis on 2% SeaKem Gold agarose gels in 1×TBE running buffer (Lonza Group Ltd, Switzerland) and post-stained using GELSTAR Nucleic Acid Gel Stain (Lonza Group Ltd). This resulted in a 965 bp Aquaporin 5' RACE product, 410 bp and 480 bp TC5777 gut membrane protein 5' RACE products, and a 642 bp TC5777 gut membrane protein 3' RACE product. The resulting amplicon was excised from the agarose gel and DNA extracted and purified using QIAquick Gel Extraction Kit (Qiagen, Valencia, Calif., USA) according to manufacturer's protocol. The extracted gel product was then concentrated according to manufacturer's protocol using Pellet Paint Co-Precipitant (Novagen/EMD Chemicals Inc, Gibbstown, N.J., USA), polished, ligated and transformed with XL10 Gold Kan Ultracompetent *Escherichia coli* cells using the PCR Script Amp Cloning Kit (Stratagene/Agilent Technologies Inc, Santa Clara, Calif., USA). Individual clones were screened via. PCR using internal vector primers M13-20 and M13 Reverse with those producing a correct sized product grown in overnight cultures to make −80° C. glycerol stocks and plasmid DNA using the QIAprep Spin Miniprep Kit (Qiagen) with a QIAvac24 (Qiagen) according to manufacturer's instructions. Clones producing the correct sized restriction enzyme product were then sequenced on a 3130xl Genetic Analyzer (Applied Biosystems) using internal vector primers in both directions, specifically the standard M13-20, M13 Reverse, T3 and T7 primers. Sequences were assembled and analysis done using MacVector with Assembler version 10.0.2. Resulting consensus sequences were subjected to blastn and blastx searches.

Cloning into *Pichia pastoris*

The Aquaporin DNA insert was amplified with the ADVANTAGE 2 PCR Enzyme System (Clontech Laboratories Inc.) using 10 µg template DNA, primers KB-156 and KB-157, and a cycling profile including an initial denaturation step of 95° C. for 3 min, thirty cycles of 92° C. for 1 min, 60° C. for 30 sec, 68° C. for 1 min and a final extension at 68° C. for 7 min. These conditions produced a 597 bp product. The TC5777 gut membrane protein DNA insert was amplified in a similar fashion using primers KB-152 and KB-153. This protocol yielded a 657 bp product. Both products were purified with agarose gel electrophoresis and gel extracted as described above. DNA was prepared for ligations by restriction enzyme digestion reactions with EcoRI (Life Technologies) and NotI (Life Technologies) per manufacturer's protocol.

The EasySelect *Pichia* Expression Vectors (Life Technologies), pPICZ αA and pPIC Z C, were used with Aquaporin and TC5777 gut membrane protein, respectively. Vector DNA was restriction enzyme digested with EcoRI (Life Technologies) and NotI (Life Technologies) and purified by agarose gel electrophoresis followed by gel extraction as described above. Aquaporin EcoRI/NotI digested insert DNA was ligated into the pPICZ αA EcoRI/NotI-digested vector using the TA Cloning Kit (Life Technologies) with T4 DNA ligase [1 unit/µL] (Life Technologies) using a modified version of the TA Cloning Kit protocol. A 10 µL ligation reaction was set up consisting of 1× T4 DNA ligase reaction buffer, 137 ng Aquaporin insert, 50 ng pPICZ αA EcoRI/NotI digested vector, and 1 µL T4 DNA ligase incubated for 17 hrs at 4° C. TC5777 gut membrane protein-encoding EcoRI/NotI digested DNA was ligated into the pPICZ C EcoRI/NotI digested vector in a similar fashion using 160 ng insert DNA.

OneShot TOP10 Electrocomp cells (Life Technologies) were transformed with ligation reaction and plated on low salt LB agar (1% tryptone, 0.5% yeast extract, 0.5% sodium chloride, 1.5% agar) with 25 µg/mL ZEOCIN (Life Technologies). Resulting colonies were screened via PCR using vector primers 5'AOX1 and 3' AOX1 and DNA isolated from positive colonies using the QIAprep Spin Miniprep Kit (Qiagen) according to manufacturer's instructions. The sequence of both strands of putative positive clones was verified by DNA sequencing. Sequence analysis utilized MacVector with Assembler version 10.0.02.

Ten micrograms of each expression vector-antigen DNA combination was restriction enzyme digested with SstI (Life Technologies) to linearize the expression vector according to the EasySelect *Pichia* Expression Kit protocol (Life Technologies). A freshly prepared 80 µL aliquot of electrocompetent *P. pastoris* KM71H strain and 5 µg linearized expression vector DNA was used for transformations according to the manufacturer's instructions using the Bio-Rad Gene Pulser and Pulse Controller with pulse settings of 1.5 kV, 200Ω and 25 µFD. Transformation mixtures were plated on YPDS (1% yeast extract, 2% peptone, 2% dextrose, 1M sorbitol, 2% agar) plates containing 100 µg/mL ZEOCIN and incubated at 30° C. for four days to allow colonies to develop.

Analysis of *Pichia pastoris* Transformants

Direct screening of individual *Pichia* KM71H colonies using PCR was done by modifying the direct screening protocol from Linder et al. (1996. Direct PCR screening of *Pichia pastoris* clones. BioTechniques. 20:980-982) and the EasySelect *Pichia* Expression Kit manual. Single colonies were prepared as described in the direct screening protocol and 2.5 µL used in a 25 µL PCR including 10 mM Tris (hydroxymethyl)aminomethane hydrochloride, pH=8.3, 50 mM KCl, 2.5 mM $MgCl_2$, 0.05 mM each dNTP, 2 µM 5' AOX1 vector primer, 2 µM 3' AOX1 vector primer, 0.16 µL of a 1 vol:1 vol mix of AmpliTaq DNA polymerase (5 U/µL stock; Applied Biosystems) and TagStart antibody (1.1 µg/µL stock; Clontech). The cycling profile included a 95° C. for 5 min initial denaturation step, thirty cycles of 95° C. for 1 min, 54° C. for 1 min, 72° C. for 1 min and a final extension at 72° C. for 7 min. Aquaporin-positive colonies produced a 1192 bp band and TC5777 gut membrane protein-positive colonies produced a 990 bp band. The *Pichia* KM71H colonies were also screened using gene specific primers for each of the antigens.

Small-scale expression experiments were used to determine the optimal method and conditions for the expression of the recombinant proteins. These used similar protocols as described in the EasySelect *Pichia* Expression Kit manual using 3 mL cultures grown in BMGY (1% yeast extract, 2% peptone, 100 mM potassium phosphate pH 6.0, 1.34% Yeast nitrogen base with ammonium sulfate without amino acids, $4 \times 10^{-5}$% biotin, 1% glycerol) and BMMY media (1% yeast extract, 2% peptone, 100 mM potassium phosphate pH 6.0, 1.34% Yeast nitrogen base with ammonium sulfate without amino acids, $4 \times 10^{-5}$% biotin, 0.5% methanol). Cultures were replenished to 0.5% final methanol concentration every 24 hours.

Both the intracellular cell pellets and the secreted supernatant samples were analyzed by denaturing gel electrophoresis under reducing conditions using the NUPAGE Electrophoresis System (Life Technologies) and NUPAGE 4-12% Bis-Tris gels (Life Technologies) in the XCell SURELOCK Mini-Cell (Life Technologies) with 1× NUPAGE MOPS SDS Running Buffer (Life Technologies) according to manufacturer's instructions. Proteins were visualized by staining with Coomassie Brilliant Blue R-250 using a modified Fairbank's method (Wong et al., 2000. Heating greatly speeds Coomassie Blue staining and destaining. Biotechniques. 28:426-432). Recombinant Aquaporin was localized in the cell pellet sample with maximal expression seen after 4 days of induction growth in BMMY while the recombinant TC5777 gut membrane protein was secreted into the growth media with maximal expression seen after 16 hr of induction in BMMY.

After the optimized expression time points were determined in the small-scale expression experiments, large scale cultures were grown to produce more protein. For Aquaporin, cells were grown in 25 mL BMGY media in 500 ml baffled flasks in a shaking incubator (275 rpm) at 29° C. to an $OD_{600}$=2-6. Cells were harvested by centrifugation and resuspended in BMMH to an $OD_{600}$=1 and returned to the incubator at 29° C. with shaking to induce expression. Every 24 hrs, methanol was added to a final concentration of 0.5% to maintain induction and cells were harvested four days post-induction. The resulting supernatant was decanted and cell pellets frozen at −70° C. until protein extraction.

Total yeast intracellular protein was extracted similarly as described above for the small-scale expression cell pellets with the exception of using 50 mL Breaking Buffer and 10 cycles of 30 sec vortexing followed by 30 sec on ice. The cell pellet lysates were then frozen at −70° C. overnight and thawed followed by 10 cycles of 30 sec vortexing and 30 sec on ice. The protein solution was clarified by centrifugation and the resulting solution concentrated using Centricon Plus-70 Centrifugal Filter Devices (Millipore; 10,000 MWCO) and freezing. TC5777 gut membrane protein was grown in similar fashion, harvesting the media supernatant fraction 16 hr after induction initiation in BMMY, and concentrating in Centricon Plus-70 units.

DNA Vaccine Reagents

The Aquaporin and TC5777 gut membrane protein coding regions were prepared using PCR with the ADVANTAGE 2 PCR Enzyme System (Clontech Laboratories Inc.) manufacturer protocol and primers KB-144 and KB-145 for Aquaporin and primers KB-146 and KB-147 for TC5777 gut membrane protein. The cycling profile including an initial denaturation step of 95° C. for 3 mins, thirty cycles of 92° C. for 1 min, 64° C. for 30 sec, 68° C. for 1 min and a final extension at 68° C. for 7 min. This protocol produced a 597 bp product for Aquaporin and 657 bp product for TC5777 gut membrane protein. Amplification products were gel purified using the QIAquick Gel Extraction kit (Qiagen), concentrated using Pellet Paint Co-Precipitant (Novagen), and ligated onto the pcDNA 4/myc-His Vectors (Life Technologies). The forward and reverse primers used in the PCR include an internal PstI and XhoI site, respectively, for in-frame insertion into the pcDNA 4/myc-His vectors. Aquaporin and the TC5777 gut membrane protein coding regions were ligated into PstI/XhoI double digested pcDNA 4/myc-His vectors A and C, respectively, vector using the TA Cloning Kit (Life Technologies) with T4 DNA ligase [1 unit/µL] (Life Technologies) using a modified version of the TA Cloning Kit protocol as described above. Sequence verifications were performed as described above. The Qiagen Plasmid Giga Kit (Qiagen) was used to produce milligram quantities of plasmid DNA for the vaccine study.

Native Affinity Purification of Expressed Recombinant Protein

Recombinant protein for both antigens was purified making use of the 6×-Histidine tag and the ProBond Purification System (Life Technologies) using PROBOND nickel-chelating resin under native conditions according to manufacturer's instructions. Eluted protein was concentrated using Amicon Ultra-15 (10,000 MWCO) centrifugation units, protein quantified by the BioRad Protein Assay Kit I with bovine plasma gamma globulin protein standards, and purity verified by gel electrophoresis as described above. Protein identity was verified by mass spectrometry analysis and Western blotting, taking advantage of the c-myc and 6×His tag epitopes on the recombinant protein that are provided by the expression vector sequence. The Western-Breeze Chromogenic Kit and Anti-myc-HRP and Anti-His (C-term)-HRP antibodies (Invitrogen) were utilized with standard protocols provided by the supplier. The supplier-provided alkaline phosphatase-conjugated secondary antibody was utilized to enhance sensitivity.

Pen Trial

Controlled pen trials were conducted to evaluate the immunogenic and protective capacity of each antigen. Recombinant protein antigen was adjuvated with Montanide ISA 61 VG (Seppic, Paris) into doses of 2 ml containing 100 µg of the recombinant protein. DNA vaccine was prepared by solubilizing expression plasmid DNA in phosphate-buffered saline at 1 mg/ml and 1 ml was mixed with an equal volume of adjuvant to produce the 2 ml dose of vaccine for each injection. One-year-old Holstein calves were randomly distributed into groups of six animals each. Negative controls were injected with adjuvant/saline alone. Following a method similar to Andreotti (2006. Performance of two Bm86 antigen vaccin formulation against tick using crossbreed bovines in stall test. Rev Bras Parasitol Vet. 15:97-100), all the animals were injected intramuscularly at 0, 2 and 4 weeks. Serum samples were taken from each animal before immunization and weekly thereafter. Twenty-one days after the last injection the animals were challenged with 15,000 larvae of the Campo Grande tick strain. These larvae were delivered in three applications of 5,000 larvae each during one week, placed in separate vials onto the back of the animals. As engorged female ticks detached, they were collected once a day, weighed, and incubated at 29° C. and 85% humidity until egg laying was complete. Eggs were weighed and incubated at 29° C. and 85% humidity to allow hatching so as to determine the eclosion percentage.

Bovine Serum Collection and Analysis

Bovine blood was sampled weekly and separated serum frozen until analyzed by ELISA. For the ELISA, sera from each group were pooled according to day of collection. Microtiter plates were coated with antigen (50 µL per well of a 1 µg antigen/ml solution in 20 mM sodium carbonate buffer, pH 9.6) and incubated overnight at 4° C. Blocking with 2% bovine serum albumin in PBS-T was followed by washing five times with PBS pH 7.4. The plates were incubated for 45 min at 37° C. with 100 µL per well of immunized bovine serum diluted to 1:100 in PBS. After washing, 50 µl of rabbit anti-bovine IgG peroxidase conjugate (Sigma, St. Louis, Mo.) diluted to 1:20,000 was added and the plate incubated for 30 min at room temperature. After incubation and washing 50 µl of chromogenic substrate o-phenylenediamine (1.0 mM) was added and the reaction was stopped after 15 min by adding 50 µl of NaOH (0.2 M). A microplate reader was used to assess the results with absorbance set at 490 nm.

Statistics and Efficacy Assessment

Vaccination effects on tick biology, and efficacy were determined as described by Garcia-Garcia et al. (1999. Sequence variations in the *Boophilus microplus* Bm86 locus and implications for immunoprotection in cattle vaccinated with this antigen. Exp Applied Acarol. 23:883-895) and Andreotti (2006. ibid). Briefly, reduction rates associated with immunization relative to the unvaccinated group were determined for adult female ticks (% DT), egg-laying capacity (% DO), and fertility (% DF). Vaccine efficacy was calculated as 100×[1−(CRT×CRO×CRF)], where CRT, CRO, and CRT represent the reduction in the number of adult female ticks, egg-laying capacity, and fertility, respectively. The Mann-Whitney nonparametric test was used to compare biological data and to assess vaccine efficacy. Mean antibody levels were determined for each group and compared using ANOVA as described previously (Andreotti, 2006. ibid).

Results

The results of the vaccination trials with both the recombinant protein antigen vaccines and DNA vaccines are shown in TABLE 2.

It is understood that the foregoing detailed description is given merely by way of illustration and that modifications and variations may be made therein without departing from the spirit and scope of the invention.

TABLE 1

| Primers Used for Aquaporin and TC5777 Gut Membrane Protein Procedures | | |
|---|---|---|
| | DESCRIPTION | SEQ ID NO: |
| Aquaporin | | |
| KB-126 5' GAG CGG GCA CAT GCA GTT GTA GGC 3' | Reverse used for 5' RACE | 17 |
| KB-144 5' ACTCAGCTGCAG AAG ATG GAG ATC GAG AAC CT 3' | Forward used for insertion into pcDNA 4/myc-His vectors A with PstI site | 18 |
| KB-145 5' TCACTGCTCGAG GCA CAT GCA GTT GTA GGC 3' | Reverse used for insertion into pcDNA 4/myc-His vectors A with XhoI site | 19 |
| KB-156 5' ACTCAGGAATTC ATG AAG ATC GAG AAC CT 3' | Forward used for DNA insertion into pPICZ αA with EcoRI site | 20 |
| KB-157 5' TCACTGGCGGCCGC CGG GCA CAT GCA GTT GTA GGC 3' | Reverse used for DNA insertion into pPICZ αA with NotI site | 21 |
| TC-5777 Gut Membrane Protein | | |
| KB-127 5' CTT CGG GCA TGC TGT ACG GCC TG 3' | Forward used for 3' RACE | 22 |
| KB-128 5' CTG CTA CGT GTC CCT CGA CTC GCT G 3' | Forward used for 3' RACE | 23 |

TABLE 1-continued

Primers Used for Aquaporin and TC5777 Gut Membrane Protein Procedures

| | DESCRIPTION | SEQ ID NO: |
|---|---|---|
| KB-130 5' CGA CTG CCT GAC GGC CTT GAG GAA C 3' | Reverse used for 5' RACE | 24 |
| KB-146 5' ACTCAGCTGCAG AAA ATG GCC ATC ACT TCT GTA A 3' | Forward used for insertion into pcDNA 4/myc-His vectors C with PstI site | 25 |
| KB-147 5' TCACTGCTCGAGG ACT GGG CAG TGG CAC 3' | Reverse used for insertion into pcDNA 4/myc-His vectors C with XhoI site | 26 |
| KB-152 5' ACTCAGGAATTC AAA ATG GCC ATC ACT TCT GTA A 3' | Forward used for DNA insertion into pPICZ C with EcoRI site | 27 |
| KB-153 5' TCACTGGCGGCCG C GG ACT GGG CAG TGG CAC 3' | Reverse used for DNA insertion into pPICZ C with NotI site | 28 |

TABLE 2

Data from Cattle Stall Trials Evaluating Aquaporin and TC5777 gut membrane protein for efficacy as vaccine antigens in cattle.

| Antigen Tested | NET[a] | EW[b] | EF[c] | EC[d] | Eff[e] |
|---|---|---|---|---|---|
| DNA Vaccine Trial 1 | | | | | |
| Aquaporin[f] + TC5777[f] | 0.4568 | 1.0502 | 1.0518 | 0.9201 | 54% |
| Recombinant Protein Trial 1 | | | | | |
| Aquaporin[g] | 0.2511 | 0.9416 | 0.9556 | 1.0762 | 76% |
| Recombinant Protein Trial 2 | | | | | |
| Aquaporin[g] | 0.3668 | 0.9105 | 0.9961 | 0.8211 | 73% |
| TC5777[g] | 0.4313 | 0.9342 | 1.0341 | 0.8797 | 63% |
| Aquaporin[h] + TC5777[h] | 0.4167 | 0.8902 | 1.0067 | 0.7887 | 71% |

[a]NET = Reduction in tick numbers = Total number of ticks from the immunized group/Total number of ticks from the control group
[b]EW = Reduction in eggs per female = (Total weight of eggs from the immunized group/Total number of ticks from immunized group)/(Total weight of eggs from the control group/Total number of ticks from control group)
[c]EF = Reduction in eggs per weight of females = (Total weight of eggs from the immunized group/Total weight of ticks from immunized group)/(Total weight of eggs from the control group/Total weight of ticks from control group)
[d]EC = Reduction in hatchability = % hatch from immunized group/% hatch from control group
[e]Eff = % Overall efficacy compared to controls = 100 [1 − (NET × EW × EF × EC)]
[f]500 micrograms of expression plasmid DNA per dose
[g]100 micrograms of recombinant protein per dose
[h]50 micrograms of recombinant protein per dose

We claim:

1. A composition comprising TC5777 gut membrane protein of the cattle tick, *Rhipicephalus microplus*, and a pharmaceutically acceptable carrier, wherein said pharmaceutically acceptable carrier is selected from the group consisting of physiological saline, phosphate buffered saline, mineral oil, vegetable oil, aqueous carboxymethyl cellulose, and polyvinylpyrrolidone; wherein said TC5777 is in an amount effective to stimulate a protective immune response in bovine to said cattle tick, and wherein said TC5777 comprises SEQ ID NO: 9.

2. A method for reducing the incidence of infestation of bovine with the cattle tick, *Rhipicephalus microplus*, comprising administering the composition of claim 1 to said bovine.

3. The method of claim 2 wherein said composition further comprises aquaporin protein, and said aquaporin protein comprises amino acids 3-198 of SEQ ID NO: 1.

4. The method of claim 2 wherein said amount of said TC5777 is greater than 10 μg per dose.

5. The method of claim 2 wherein said composition further comprises an adjuvant.

6. The composition of claim 1 wherein said amount of said TC5777 is greater than 10 μg per dose.

7. The composition of claim 6, wherein said amount of said TC5777 is between about 50 μg to about 150 per μg per dose.

8. The composition of claim 1 further comprising an adjuvant.

9. The composition of claim 8, wherein said adjuvant is selected from the group consisting of mineral oil, vegetable oil, alum, Freund's incomplete adjuvant, and microparticles, nanoparticles or beads of a biocompatible matrix material.

10. The composition of claim 9, wherein said biocompatible matrix material comprises agar or polyacrylate.

11. The composition of claim 1, wherein said carrier is phosphate buffered saline.

12. A composition comprising TC5777 gut membrane protein of the cattle tick, *Rhipicephalus microplus*, a pharmaceutically acceptable carrier, and an adjuvant; wherein said TC5777 is in an amount effective to stimulate a protective immune response in bovine to said cattle tick; wherein said TC5777 comprises SEQ ID NO: 9; and wherein said adjuvant is selected from the group consisting of mineral oil, vegetable oil, alum, Freund's incomplete adjuvant, and microparticles, nanoparticles or beads of a biocompatible matrix material.

13. The composition of claim 12, wherein said biocompatible matrix material comprises agar or polyacrylate.

14. The composition of claim 12 wherein said amount of said TC5777 is greater than 10 μg per dose.

15. The composition of claim 12 wherein said amount of said TC5777 is between about 50 μg to about 150 per μg per dose.

16. The composition of claim 12, wherein said pharmaceutically acceptable carrier is selected from the group consisting of physiological saline, phosphate buffered saline, aqueous carboxymethyl cellulose, and polyvinylpyrrolidone.

* * * * *

SEQUENCE LISTING

<160> NUMBER OF SEQ ID NOS: 28

<210> SEQ ID NO 1
<211> LENGTH: 200
<212> TYPE: PRT
<213> ORGANISM: Rhipicephalus microplus

<400> SEQUENCE: 1

```
Met Lys Ile Glu Asn Leu Leu Ile Arg Gln Leu Ile Asn Glu Phe Leu
1               5                   10                  15

Gly Thr Met Ile Leu Ile Thr Ile Gly Asp Ser Ile Met Ala Ile Ile
            20                  25                  30

Ile Ala Gly Asp Asn Glu Ser Leu Ala Ala Cys Val Gly Pro Leu Gly
        35                  40                  45

Trp Gly Val Ala Ile Tyr Val Ala Val Gln Ile Ser Gly Gly Val Ser
    50                  55                  60
```

```
Ser His Leu Asn Pro Ala Val Thr Leu Ala Gln Ala Ser Val Arg Lys
 65                  70                  75                  80

Phe Pro Ile Ala Lys Val Pro Leu Tyr Phe Ala Gln Tyr Leu Gly
             85                  90                  95

Gly Phe Val Gly Ala Ala Leu Val Phe Ala Thr Tyr Lys Asp Ala Ile
            100                 105                 110

Glu His Phe Asp Gln Gly Ile Arg Gln Val Thr Gly Glu Lys Ala Thr
            115                 120                 125

Ala Gly Ile Phe Ala Thr Tyr Pro Arg Pro His Val Ser Thr Leu Thr
        130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175

His Pro Ile Cys Leu Gly Leu Met Ile Met Ala Ile Ile Phe Ser Phe
            180                 185                 190

Ala Tyr Asn Cys Met Cys Pro Leu
            195                 200

<210> SEQ ID NO 2
<211> LENGTH: 317
<212> TYPE: PRT
<213> ORGANISM: Rhipicephalus microplus

<400> SEQUENCE: 2

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Glu Phe Met Lys Ile Glu Asn
             85                  90                  95

Leu Leu Ile Arg Gln Leu Ile Asn Glu Phe Leu Gly Thr Met Ile Leu
            100                 105                 110

Ile Thr Ile Gly Asp Ser Ile Met Ala Ile Ile Ala Gly Asp Asn
            115                 120                 125

Glu Ser Leu Ala Ala Cys Val Gly Pro Leu Gly Trp Gly Val Ala Ile
        130                 135                 140

Tyr Val Ala Val Gln Ile Ser Gly Gly Val Ser Ser His Leu Asn Pro
145                 150                 155                 160

Ala Val Thr Leu Ala Gln Ala Ser Val Arg Lys Phe Pro Ile Ala Lys
                165                 170                 175

Val Pro Leu Tyr Phe Ala Ala Gln Tyr Leu Gly Gly Phe Val Gly Ala
            180                 185                 190

Ala Leu Val Phe Ala Thr Tyr Lys Asp Ala Ile Glu His Phe Asp Gln
            195                 200                 205

Gly Ile Arg Gln Val Thr Gly Glu Lys Ala Thr Ala Gly Ile Phe Ala
        210                 215                 220

Thr Tyr Pro Arg Pro His Val Ser Thr Leu Thr Cys Phe Ile Asp Gln
225                 230                 235                 240
```

```
Val Ile Ala Thr Gly Ile Met Met Val Cys Val Glu Ala Ile Gly Asp
                245                 250                 255

Thr Arg Asn Phe Gly Gly Ile Pro Pro His Ile His Pro Ile Cys Leu
            260                 265                 270

Gly Leu Met Ile Met Ala Ile Ile Phe Ser Phe Ala Tyr Asn Cys Met
            275                 280                 285

Cys Pro Ala Ala Ala Ser Phe Leu Glu Gln Lys Leu Ile Ser Glu Glu
            290                 295                 300

Asp Leu Asn Ser Ala Val Asp His His His His His His
305                 310                 315
```

<210> SEQ ID NO 3
<211> LENGTH: 226
<212> TYPE: PRT
<213> ORGANISM: Rhipicephalus microplus

<400> SEQUENCE: 3

```
Met Glu Ile Glu Asn Leu Leu Ile Arg Gln Leu Ile Asn Glu Phe Leu
1               5                   10                  15

Gly Thr Met Ile Leu Ile Thr Ile Gly Asp Ser Ile Met Ala Ile Ile
            20                  25                  30

Ile Ala Gly Asp Asn Glu Ser Leu Ala Ala Cys Val Gly Pro Leu Gly
            35                  40                  45

Trp Gly Val Ala Ile Tyr Val Ala Val Gln Ile Ser Gly Gly Val Ser
    50                  55                  60

Ser His Leu Asn Pro Ala Val Thr Leu Ala Gln Ala Ser Val Arg Lys
65                  70                  75                  80

Phe Pro Ile Ala Lys Val Pro Leu Tyr Phe Ala Ala Gln Tyr Leu Gly
                85                  90                  95

Gly Phe Val Gly Ala Ala Leu Val Phe Ala Thr Tyr Lys Asp Ala Ile
            100                 105                 110

Glu His Phe Asp Gln Gly Ile Arg Gln Val Thr Gly Glu Lys Ala Thr
            115                 120                 125

Ala Gly Ile Phe Ala Thr Tyr Pro Arg Pro His Val Ser Thr Leu Thr
        130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175

His Pro Ile Cys Leu Gly Leu Met Ile Met Ala Ile Ile Phe Ser Phe
            180                 185                 190

Ala Tyr Asn Cys Met Cys Leu Glu Ser Arg Gly Pro Phe Glu Gln Lys
        195                 200                 205

Leu Ile Ser Glu Glu Asp Leu Asn Met His Thr Gly His His His His
    210                 215                 220

His His
225
```

<210> SEQ ID NO 4
<211> LENGTH: 198
<212> TYPE: PRT
<213> ORGANISM: Rhipicephalus microplus

<400> SEQUENCE: 4

```
Met Glu Ile Glu Asn Leu Leu Ile Arg Gln Leu Ile Asn Glu Phe Leu
1               5                   10                  15
```

Gly Thr Met Ile Leu Ile Thr Ile Gly Asp Ser Ile Met Ala Ile Ile
            20                  25                  30

Ile Ala Gly Asp Asn Glu Ser Leu Ala Ala Cys Val Gly Pro Leu Gly
        35                  40                  45

Trp Gly Val Ala Ile Tyr Val Ala Val Gln Ile Ser Gly Gly Val Ser
    50                  55                  60

Ser His Leu Asn Pro Ala Val Thr Leu Ala Gln Ala Ser Val Arg Lys
65                  70                  75                  80

Phe Pro Ile Ala Lys Val Pro Leu Tyr Phe Ala Ala Gln Tyr Leu Gly
                85                  90                  95

Gly Phe Val Gly Ala Ala Leu Val Phe Ala Thr Tyr Lys Asp Ala Ile
            100                 105                 110

Glu His Phe Asp Gln Gly Ile Arg Gln Val Thr Gly Glu Lys Ala Thr
        115                 120                 125

Ala Gly Ile Phe Ala Thr Tyr Pro Arg Pro His Val Ser Thr Leu Thr
130                 135                 140

Cys Phe Ile Asp Gln Val Ile Ala Thr Gly Ile Met Met Val Cys Val
145                 150                 155                 160

Glu Ala Ile Gly Asp Thr Arg Asn Phe Gly Gly Ile Pro Pro His Ile
                165                 170                 175

His Pro Ile Cys Leu Gly Leu Met Ile Met Ala Ile Ile Phe Ser Phe
            180                 185                 190

Ala Tyr Asn Cys Met Cys
            195

<210> SEQ ID NO 5
<211> LENGTH: 947
<212> TYPE: DNA
<213> ORGANISM: Rhipicephalus microplus

<400> SEQUENCE: 5
aagcagtggt atcaacgcag agtacgcggg ggggctggga aaagctgcta gcatcaactc      60
ggcttctagc ttggggtctc gcaccgcgcc tcgagcccga ccagcctgcg gtggcgccgt     120
ctcgctgaaa gggggaaaga ggaaagagaa agaagaaaag aaaaatatcg ccggcatcgg     180
cgacgaaggc ggagcagcaa tgcgatcgtc agagcacgca tttcgacggt gagattcgga     240
agctcgaagg cgtcgccggc actgcgagaa agccggtgaa gtactttggg accgccgcgt     300
aggcgtcttg acagtccgct cccgaggcaa cgacgacacg ctccaagatg aagatcgaga     360
acctgctcat acggcagctc atcaacgagt tcctcggaac aatgattcta attactatcg     420
gcgactccat catggccatc atcatcgccg gtgacaacga gtctctggct gcttgcgtgg     480
ggcccttggg atgggcgtc gccatctacg tggccgtgca aatctccgga ggagtctcgt     540
cccacctgaa tcctgccgtg acgctggccc aggcgtccgt gcgcaagttt ccgatcgcca     600
aagtgccgct atacttcgcg gctcagtacc tgggtggctt cgtcggtgcg gcgctcgtgt     660
ttgccaccta caaagacgct attgaacact cgaccaggg aatccgccaa gtgacgggag     720
agaaggccac ggctggtata tttgcaactt accccagacc acacgtctcc actctgacct     780
gcttcattga tcaggtcatc gcaacgggca taatgatggt gtgcgtcgag gccatcggcg     840
acactcgcaa cttcggcggc attccgccgc acattcaccc aatctgcttg ggtctcatga     900
tcatggctat tatcttcagt ttcgcctaca actgcatgtg cccgctc                   947

<210> SEQ ID NO 6

```
<211> LENGTH: 954
<212> TYPE: DNA
<213> ORGANISM: Rhipicephalus microplus

<400> SEQUENCE: 6
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaaggggta     240
tctctcgaga aaagagaggc tgaagctgaa ttcatgaaga tcgagaacct gctcatacgg     300
cagctcatca acgagttcct cggaacaatg attctaatta ctatcggcga ctccatcatg     360
gccatcatca tcgccggtga caacgagtct ctggctgctt gcgtggggcc cttgggatgg     420
ggcgtcgcca tctacgtggc cgtgcaaatc tccggaggag tctcgtccca cctgaatcct     480
gccgtgacgc tggcccaggc gtccgtgcgc aagtttccga tcgccaaagt gccgctatac     540
ttcgcggctc agtacctggg tggcttcgtc ggtgcggcgc tcgtgtttgc cacctacaaa     600
gacgctattg aacacttcga ccagggaatc cgccaagtga cgggagagaa ggccacggct     660
ggtatatttg caacttaccc cagaccacac gtctccactc tgacctgctt cattgatcag     720
gtcatcgcaa cgggcataat gatggtgtgc gtcgaggcca tcggcgacac tcgcaacttc     780
ggcggcattc cgccgcacat tcacccaatc tgcttgggtc tcatgatcat ggctattatc     840
ttcagtttcg cctacaactg catgtgcccg gcggccgcca gctttctaga acaaaaactc     900
atctcagaag aggatctgaa tagcgccgtc gaccatcatc atcatcatca ttga           954

<210> SEQ ID NO 7
<211> LENGTH: 684
<212> TYPE: DNA
<213> ORGANISM: Rhipicephalus microplus

<400> SEQUENCE: 7
aagatggaga tcgagaacct gctcatacgg cagctcatca acgagttcct cggaacaatg      60
attctaatta ctatcggcga ctccatcatg gccatcatca tcgccggtga caacgagtct     120
ctggctgctt gcgtggggcc cttgggatgg ggcgtcgcca tctacgtggc cgtgcaaatc     180
tccggaggag tctcgtccca cctgaatcct gccgtgacgc tggcccaggc gtccgtgcgc     240
aagtttccga tcgccaaagt gccgctatac ttcgcggctc agtacctggg tggcttcgtc     300
ggtgcggcgc tcgtgtttgc cacctacaaa gacgctattg aacacttcga ccagggaatc     360
cgccaagtga cgggagagaa ggccacggct ggtatatttg caacttaccc cagaccacac     420
gtctccactc tgacctgctt cattgatcag gtcatcgcaa cgggcataat gatggtgtgc     480
gtcgaggcca tcggcgacac tcgcaacttc ggcggcattc cgccgcacat tcacccaatc     540
tgcttgggtc tcatgatcat ggctattatc ttcagtttcg cctacaactg catgtgcctc     600
gagtctagag ggcccttcga acaaaaactc atctcagaag aggatctgaa tatgcatacc     660
ggtcatcatc accatcacca ttga                                            684

<210> SEQ ID NO 8
<211> LENGTH: 595
<212> TYPE: DNA
<213> ORGANISM: Rhipicephalus microplus

<400> SEQUENCE: 8 atgagatcg agaacctgct catacggcag ctcatcaacg agttcctcgg aacaatgatt       60
```

```
ctaattacta tcggcgactc catcatggcc atcatcatcg ccggtgacaa cgagtctctg    120
gctgcttgcg tggggccctt gggatggggc gtcgccatct acgtggccgt gcaaatctcc    180
ggaggagtct cgtcccacct gaatcctgcc gtgacgctgg cccaggcgtc cgtgcgcaag    240
tttccgatcg ccaaagtgcc gctatacttc gcggctcagt acctgggtgg cttcgtcggt    300
gcggcgctcg tgtttgccac ctacaaagac gctattgaac acttcgacca gggaatccgc    360
caagtgacgg gagagaaggc cacggctggt atatttgcaa cttaccccag accacacgtc    420
tccactctga cctgcttcat tgatcaggtc atcgcaacgg cataatgat ggtgtgcgtc     480 gaggccatcg gcgacactcg caacttcggc ggcattccgc cgcacattca cccaatctgc    540
ttgggtctca tgatcatggc tattatcttc agtttcgcct acaactgcat gtgcc         595
```

<210> SEQ ID NO 9
<211> LENGTH: 219
<212> TYPE: PRT
<213> ORGANISM: Rhipicephalus microplus

<400> SEQUENCE: 9

```
Met Ala Ile Thr Ser Val Ile Thr Leu Ser Leu Leu Val Val Gly Ala
1               5                   10                  15

Leu Ala Gly Ser Lys Gln Asp Ala Asn Asn Tyr Ile Asp Thr Val Leu
            20                  25                  30

Arg Asp His Leu Pro Ala Asn Val Arg Ser Leu Asn Leu Asp Pro Thr
        35                  40                  45

His Leu Pro Gly Phe Asn Phe Lys Val Asp Ser Thr Gly Pro Thr Asn
    50                  55                  60

Arg Asp Leu Lys Ala Gln Phe Pro Ser Gly Met Leu Tyr Gly Leu Ser
65                  70                  75                  80

Ser Val Val Arg Arg Gly Asp Cys Gly Val Pro Gly Trp Gln Gly
                85                  90                  95

Ser Ser Val Thr Thr Gly Cys Tyr Val Ser Leu Asp Ser Leu Arg Leu
            100                 105                 110

Thr Phe Asp Gly Ser Val Ser Gly Tyr Ser Leu Leu Gly Gly Lys Lys
        115                 120                 125

Asn Val Ser Leu Asp Leu Val Val Glu Lys Thr Asn Ala Phe Val Glu
    130                 135                 140

Ala Thr Ala Pro Phe Gly Gln Gln Ala Thr Leu Lys Thr Leu Thr Leu
145                 150                 155                 160

Ser Gly Ile Glu Phe Arg Val Asn Val Asn Lys Lys Leu Glu Leu Asn
                165                 170                 175

Asp Lys Arg Glu Lys Lys Phe Leu Lys Ala Val Arg Gln Ser Ala Ser
            180                 185                 190

Asn Ile Leu Leu Gly Ile Val Asn Ser Ser Phe Arg Glu Ala Leu Ser
        195                 200                 205

Arg Ser Val Ser Lys Val Pro Leu Pro Ser Pro
    210                 215
```

<210> SEQ ID NO 10
<211> LENGTH: 246
<212> TYPE: PRT
<213> ORGANISM: Rhipicephalus microplus

<400> SEQUENCE: 10

```
Met Ala Ile Thr Ser Val Ile Thr Leu Ser Leu Leu Val Val Gly Ala
1               5                   10                  15
```

Leu Ala Gly Ser Lys Gln Asp Thr Asn Asn Tyr Ile Asp Thr Val Leu
            20                  25                  30

Arg Asp His Leu Pro Ala Asn Val Arg Ser Leu Asn Leu Asp Pro Thr
            35                  40                  45

His Leu Pro Gly Phe Asn Phe Lys Val Asp Ser Thr Gly Pro Thr Asn
            50                  55                  60

Arg Asp Leu Lys Ala Gln Phe Pro Ser Gly Met Leu Tyr Gly Leu Ser
65                  70                  75                  80

Ser Val Val Arg Arg Arg Gly Asp Cys Gly Val Pro Gly Trp Gln Gly
                85                  90                  95

Ser Ser Val Thr Thr Gly Cys Tyr Val Ser Leu Asp Ser Leu Arg Leu
            100                 105                 110

Thr Phe Asp Gly Ser Val Ser Gly Tyr Ser Leu Leu Gly Gly Lys Lys
            115                 120                 125

Asn Val Ser Leu Asp Leu Val Val Glu Lys Thr Asn Ala Phe Val Glu
            130                 135                 140

Ala Thr Ala Pro Phe Gly Gln Gln Ala Thr Leu Lys Thr Leu Thr Leu
145                 150                 155                 160

Ser Gly Ile Glu Phe Arg Val Asn Val Asn Lys Lys Leu Glu Leu Asn
                165                 170                 175

Asp Lys Arg Glu Lys Lys Phe Leu Lys Ala Val Arg Gln Ser Ala Ser
            180                 185                 190

Asn Ile Leu Leu Gly Ile Val Asn Ser Ser Phe Arg Glu Ala Leu Ser
            195                 200                 205

Arg Ser Val Ser Lys Val Pro Leu Pro Ser Pro Arg Pro Pro Ala Tyr
            210                 215                 220

Val Glu Gln Lys Leu Ile Ser Glu Glu Asp Leu Asn Ser Ala Val Asp
225                 230                 235                 240

His His His His His His
            245

<210> SEQ ID NO 11
<211> LENGTH: 246
<212> TYPE: PRT
<213> ORGANISM: Rhipicephalus microplus

<400> SEQUENCE: 11

Met Ala Ile Thr Ser Val Ile Thr Leu Ser Leu Leu Val Val Gly Ala
1               5                   10                  15

Leu Ala Gly Ser Lys Gln Asp Thr Asn Asn Tyr Ile Asp Thr Val Leu
            20                  25                  30

Arg Asp His Leu Pro Ala Asn Val Arg Ser Leu Asn Leu Asp Pro Thr
            35                  40                  45

His Leu Pro Gly Phe Asn Phe Lys Val Asp Ser Thr Gly Pro Thr Asn
            50                  55                  60

Arg Asp Leu Lys Ala Gln Phe Pro Ser Gly Met Leu Tyr Gly Leu Ser
65                  70                  75                  80

Ser Val Val Arg Arg Arg Gly Asp Cys Gly Val Pro Gly Trp Gln Gly
                85                  90                  95

Ser Ser Val Thr Thr Gly Cys Tyr Val Ser Leu Asp Ser Leu Arg Leu
            100                 105                 110

Thr Phe Asp Gly Ser Val Ser Gly Tyr Ser Leu Leu Gly Gly Lys Lys
            115                 120                 125

Asn Val Ser Leu Asp Leu Val Val Glu Lys Thr Asn Ala Phe Val Glu

-continued

```
                 130                 135                 140
Ala Thr Ala Pro Phe Gly Gln Gln Ala Thr Leu Lys Thr Leu Thr Leu
145                 150                 155                 160

Ser Gly Ile Glu Phe Arg Val Asn Val Asn Lys Lys Leu Glu Leu Asn
                165                 170                 175

Asp Lys Arg Glu Lys Lys Phe Leu Lys Ala Val Arg Gln Ser Ala Ser
            180                 185                 190

Asn Ile Leu Leu Gly Ile Val Asn Ser Ser Phe Arg Glu Ala Leu Ser
        195                 200                 205

Arg Ser Val Ser Lys Val Pro Leu Pro Ser Pro Arg Pro Pro Ala Tyr
    210                 215                 220

Val Glu Gln Lys Leu Ile Ser Glu Glu Asp Leu Asn Ser Ala Val Asp
225                 230                 235                 240

His His His His His His
            245

<210> SEQ ID NO 12
<211> LENGTH: 825
<212> TYPE: DNA
<213> ORGANISM: Rhipicephalus microplus

<400> SEQUENCE: 12
aagcagtggt atcaacgcag agtacgcggg gacagagctc ggggaagacg ccgtgaaagg      60
ttgctgcaca aaatggccat cacttctgta atcaccttga gtctgcttgt cgtcggcgca     120
ctcgctggct ccaagcagga tgccaacaac tacatcgaca cggtgcttcg cgaccaccta     180
ccggccaacg tgcgttcgct caacctggac ccgactcact tgccgggttt caacttcaag     240
gtcgactcga ctggcccgac caaccgggac ctgaaggcgc agttcccttc gggcatgctg     300
tacggcctgt cgagcgtggt gcgccgtcgc ggcgactgcg cgtaccgggc tggcagggc     360 tcgagcgtca ccactggctg ctacgtgtcc ctcgactcgc tgcgactcac cttcgacgga     420
agcgtaagcg gctacagcct tctcggtggc aaaaagaacg tcagcctcga cctggtcgtc     480
gagaagacca tgccttcgt tgaggccacg gcacccttcg gtcagcaagc gacgctgaag     540
acgctcacct tgagcggcat cgagttccgc gtgaacgtga acaagaagct cgaattgaac     600
gacaagcgcg agaagaagtt cctcaaggcc gtcaggcagt cggcgagcaa catccttctg     660
ggcatcgtga actcatccct ccgcgaggct ctcagccgct ccgtgagcaa ggtgccactg     720
cccagtccat gaaaaaaaaa aaaaaaaaaa aaaaaaaaaa aacccaagga gaaatacgaa     780
caacgacgaa ttgaaataaa cgacgaaacg tgctgcaatg catca                    825

<210> SEQ ID NO 13
<211> LENGTH: 741
<212> TYPE: DNA
<213> ORGANISM: Rhipicephalus microplus

<400> SEQUENCE: 13
atggccatca cttctgtaat caccttgagt ctgcttgtcg tcggtgcact cgctggctcc      60
aagcaggata ccaacaacta catcgacacg gtgcttcgcg accacctacc ggccaacgtg     120
cgttcgctca acctggaccc gactcacttg ccgggtttca acttcaaggt cgactcgact     180
ggtccgacca accgggacct gaaggcgcag ttcccttcgg gcatgctgta cggcctgtcg     240
agcgtggtgc gccgtcgcgg cgattgcggc gttccgggct ggcagggctc gagcgtcacc     300
actggctgct acgtgtccct cgactcgctg cgactcacct tcgacggaag cgtaagcggc     360
```

| | |
|---|---|
| tacagccttc tcggtggcaa aaagaacgtc agcctcgacc tggtcgtcga agaccaat | 420 |
| gccttcgttg aggccacggc acccttcggt cagcaagcga cgctgaagac gctcaccttg | 480 |
| agcggcatcg agttccgcgt gaacgtgaac aagaagctcg aattgaacga caagcgcgag | 540 |
| aagaagttcc tcaaggccgt caggcagtcg gcgagcaaca tccttctggg catcgtgaac | 600 |
| tcatccttcc gcgaggctct cagccgctcc gtgagcaagg tgccactgcc cagtccgcgg | 660 |
| ccgccagctt acgtagaaca aaaactcatc tcagaagagg atctgaatag cgccgtcgac | 720 |
| catcatcatc atcatcattg a | 741 |

<210> SEQ ID NO 14
<211> LENGTH: 741
<212> TYPE: DNA
<213> ORGANISM: Rhipicephalus microplus

<400> SEQUENCE: 14

| | |
|---|---|
| aaaatggcca tcacttctgt aatcaccttg agtctgcttg tcgtcggtgc actcgctggc | 60 |
| tccaagcagg ataccaacaa ctacatcgac acggtgcttc gcgaccacct accggccaac | 120 |
| gtgcgttcgc tcaacctgga cccgactcac ttgccgggtt tcaacttcaa ggtcgactcg | 180 |
| actggtccga ccaaccggga cctgaaggcg cagttcccct cgggcatgct gtacggcctg | 240 |
| tcgagcgtgg tgcgccgtcg cggcgattgc ggcgttccgg ctggcaggg ctcgagcgtc | 300 |
| accactggct gctacgtgtc cctcgactcg ctgcgactca ccttcgacgg aagcgtaagc | 360 |
| ggctacagcc ttctcggtgg caaaaagaac gtcagcctcg acctggtcgt cgagaagacc | 420 |
| aatgccttcg ttgaggccac ggcacccttc ggtcagcaag cgacgctgaa gacgctcacc | 480 |
| ttgagcggca tcgagttccg cgtgaacgtg aacaagaagc tcgaattgaa cgacaagcgc | 540 |
| gagaagaagt tcctcaaggc cgtcaggcag tcggcgagca catccttct gggcatcgtg | 600 |
| aactcatcct tccgcgaggc tctcagccgc tccgtgagca aggtgccact gcccagtcct | 660 |
| cgaggtcacc cattcgaaca aaaactcatc tcagaagagg atctgaatat gcataccggt | 720 |
| catcatcacc atcaccattg a | 741 |

<210> SEQ ID NO 15
<211> LENGTH: 595
<212> TYPE: DNA
<213> ORGANISM: Rhipicephalus microplus

<400> SEQUENCE: 15

| | |
|---|---|
| atgaagattg agaacttgtt gattagacaa ttgattaacg agttcttggg tactatgatt | 60 |
| ttgattacta ttggtgactc tattatggct attattattg ctggtgacaa cgagtctttg | 120 |
| gctgcttgcg ttggtccatt gggttggggt gttgctattt acgttgctgt tcaaatttct | 180 |
| ggtggtgttt cttctcactt gaatccagct gttactttgg ctcaagcttc tgttagaaag | 240 |
| tttccaattg ctaaagttcc attgtacttc gctgctcaat acttgggtgg tttcgttggt | 300 |
| gctgctttgg tttttgctac ttacaaagac gctattgaac acttcgacca aggtattaga | 360 |
| caagttactg gtgagaaggc tactgctggt attttttgcta cttacccaag accacacgtt | 420 |
| tctactttga cttgcttcat tgatcaagtt attgctactg gtattatgat ggtttgcgtt | 480 |
| gaggctattg gtgacactag aaacttcggt ggtattccac cacacattca cccaatttgc | 540 |
| ttgggtttga tgattatggc tattattttc tctttcgctt acaactgcat gtgcc | 595 |

<210> SEQ ID NO 16
<211> LENGTH: 656

<212> TYPE: DNA
<213> ORGANISM: Rhipicephalus microplus

<400> SEQUENCE: 16

```
atggctatta cttctgttat tactttgtct tgttggttg ttggtgcttt ggctggttct      60
aagcaagatg ctaacaacta cattgacact gttttgagag accacttgcc agctaacgtt    120
agatctttga acttggaccc aactcacttg ccaggtttca acttcaaggt tgactctact    180
ggtccaacta acagagactt gaaggctcaa ttcccatctg gtatgttgta cggtttgtct    240
tctgttgtta agaagagg tgactgcggt gttccaggtt ggcaaggttc ttctgttact     300
actggttgct acgtttcttt ggactctttg agattgactt cgacggttc tgtttctggt     360
tactctttgt tgggtggtaa aagaacgtt tctttggact tggttgttga agactaat       420
gctttcgttg aggctactgc tccattcggt caacaagcta ctttgaagac tttgactttg    480
tctggtattg agttcagagt taacgttaac aagaagttgg aattgaacga caagagagag    540
aagaagttct tgaaggctgt tagacaatct gcttctaaca ttttgttggg tattgttaac    600
tcttctttca gagaggcttt gtctagatct gtttctaagg ttccattgcc atctcc        656
```

<210> SEQ ID NO 17
<211> LENGTH: 24
<212> TYPE: DNA
<213> ORGANISM: Rhipicephalus microplus

<400> SEQUENCE: 17

```
gagcgggcac atgcagttgt aggc                                            24
```

<210> SEQ ID NO 18
<211> LENGTH: 32
<212> TYPE: DNA
<213> ORGANISM: Rhipicephalus microplus

<400> SEQUENCE: 18

```
actcagctgc agaagatgga gatcgagaac ct                                   32
```

<210> SEQ ID NO 19
<211> LENGTH: 30
<212> TYPE: DNA
<213> ORGANISM: Rhipicephalus microplus

<400> SEQUENCE: 19

```
tcactgctcg aggcacatgc agttgtaggc                                      30
```

<210> SEQ ID NO 20
<211> LENGTH: 29
<212> TYPE: DNA
<213> ORGANISM: Rhipicephalus microplus

<400> SEQUENCE: 20

```
actcaggaat tcatgaagat cgagaacct                                       29
```

<210> SEQ ID NO 21
<211> LENGTH: 35
<212> TYPE: DNA
<213> ORGANISM: Rhipicephalus microplus

<400> SEQUENCE: 21

```
tcactggcgg ccgccgggca catgcagttg taggc                                35
```

<210> SEQ ID NO 22

```
<211> LENGTH: 23
<212> TYPE: DNA
<213> ORGANISM: Rhipicephalus microplus

<400> SEQUENCE: 22
cttcgggcat gctgtacggc ctg                                              23

<210> SEQ ID NO 23
<211> LENGTH: 25
<212> TYPE: DNA
<213> ORGANISM: Rhipicephalus microplus

<400> SEQUENCE: 23
ctgctacgtg tccctcgact cgctg                                            25

<210> SEQ ID NO 24
<211> LENGTH: 25
<212> TYPE: DNA
<213> ORGANISM: Rhipicephalus microplus

<400> SEQUENCE: 24
cgactgcctg acggccttga ggaac                                            25

<210> SEQ ID NO 25
<211> LENGTH: 34
<212> TYPE: DNA
<213> ORGANISM: Rhipicephalus microplus

<400> SEQUENCE: 25
actcagctgc agaaaatggc catcacttct gtaa                                  34

<210> SEQ ID NO 26
<211> LENGTH: 28
<212> TYPE: DNA
<213> ORGANISM: Rhipicephalus microplus

<400> SEQUENCE: 26
tcactgctcg aggactgggc agtggcac                                         28

<210> SEQ ID NO 27
<211> LENGTH: 34
<212> TYPE: DNA
<213> ORGANISM: Rhipicephalus microplus

<400> SEQUENCE: 27
actcaggaat tcaaaatggc catcacttct gtaa                                  34

<210> SEQ ID NO 28
<211> LENGTH: 31
<212> TYPE: DNA
<213> ORGANISM: Rhipicephalus microplus

<400> SEQUENCE: 28
tcactggcgg ccgcggactg ggcagtggca c                                     31
```